US012709603B2

(12) United States Patent
Teng et al.

(10) Patent No.: US 12,709,603 B2
(45) Date of Patent: Aug. 18, 2026

(54) CRYSTALLINE FORMS OF {2-[3-CYCLOHEXYL-3-(TRANS-4-PROPOXY-CYCLOHEXYL)-UREIDO]-THIAZOL-5-YLSULFANYL}-ACETIC ACID AND USES THEREOF

(71) Applicant: vTv Therapeutics LLC, High Point, NC (US)

(72) Inventors: Jing Teng, Lafayette, IN (US); Yizheng Cao, Lafayette, IN (US)

(73) Assignee: VTV THERAPEUTICS LLC, High Point, NC (US)

( * ) Notice: Subject to any disclaimer, the term of this patent is extended or adjusted under 35 U.S.C. 154(b) by 423 days.

(21) Appl. No.: 18/000,908

(22) PCT Filed: Jun. 7, 2021

(86) PCT No.: PCT/US2021/036082

§ 371 (c)(1),
(2) Date: Dec. 6, 2022

(87) PCT Pub. No.: WO2021/252309

PCT Pub. Date: Dec. 16, 2021

(65) Prior Publication Data

US 2023/0219910 A1 Jul. 13, 2023

Related U.S. Application Data

(60) Provisional application No. 63/035,994, filed on Jun. 8, 2020.

(51) Int. Cl.
*C07D 277/54* (2006.01)
*A61K 31/426* (2006.01)

(52) U.S. Cl.
CPC .......... *C07D 277/54* (2013.01); *A61K 31/426* (2013.01); *C07B 2200/13* (2013.01)

(58) Field of Classification Search
CPC ..... C07D 277/54; C07B 2200/13; A61P 3/06; A61P 9/12; A61P 3/10; A61K 31/426
(Continued)

(56) References Cited

U.S. PATENT DOCUMENTS 7,384,967 B2 6/2008 Polisetti et al.
7,432,287 B2 10/2008 Iino et al.
(Continued)

FOREIGN PATENT DOCUMENTS

AU 2993771 A 12/1972
CA 2416229 A1 1/2002
(Continued)

OTHER PUBLICATIONS

Anderson, Bradley D. et al. Chapter 34: Preparation of water-soluble organic compounds by salt formation. Latest Drug Discovery Chemistry 2:347-365 (1999).
(Continued)

*Primary Examiner* — Taylor V Oh
(74) *Attorney, Agent, or Firm* — WILSON SONSINI GOODRICH & ROSATI

(57) ABSTRACT

The present disclosure relates to a) crystalline forms of {2-[3-cyclohexyl-3-(trans-4-propoxy-cyclohexyl)-ureido]-thiazo 1-5-ylsulfanyl}-acetic acid ("Compound I"); b) pharmaceutical compositions, comprising one or more crystalline forms of Compound I, and optionally, a pharmaceutically acceptable carrier; c) methods of treating a type of diabetes mellitus or other disorders by administering one or more crystalline forms of Compound I; and d) methods for the preparation of crystalline forms of Compound I.

5 Claims, 27 Drawing Sheets

(58) Field of Classification Search
USPC .......................................................... 514/369
See application file for complete search history.

(56) References Cited

U.S. PATENT DOCUMENTS

| | | | |
|---|---|---|---|
| 7,582,769 | B2 | 9/2009 | Murray et al. |
| 7,598,391 | B2 | 10/2009 | Murray et al. |
| 7,851,636 | B2 | 12/2010 | Murray et al. |
| 7,872,139 | B2 | 1/2011 | Murray et al. |
| 7,884,210 | B2 | 2/2011 | Lau et al. |
| 7,897,628 | B2 | 3/2011 | Polisetti et al. |
| 8,063,081 | B2 | 11/2011 | Polisetti et al. |
| 8,263,634 | B2 | 9/2012 | Murray et al. |
| 8,283,834 | B2 | 10/2012 | Matsubara et al. |
| 8,318,778 | B2 | 11/2012 | Murray et al. |
| 8,362,049 | B2 | 1/2013 | Murray et al. |
| 8,586,614 | B2 | 11/2013 | Lau et al. |
| RE45,325 | E | 1/2015 | Anderson et al. |
| RE45,670 | E | 9/2015 | Polisetti et al. |
| 9,359,313 | B2 | 6/2016 | Mjalli et al. |
| 9,855,251 | B2 | 1/2018 | Mjalli et al. |
| 10,004,782 | B2 | 6/2018 | Valcarce et al. |
| 10,064,846 | B2 | 9/2018 | Mjalli et al. |
| 10,363,244 | B2 | 7/2019 | Mjalli et al. |
| 10,588,943 | B2 | 3/2020 | Valcarce et al. |
| 10,952,993 | B2 | 3/2021 | Freeman et al. |
| 10,980,861 | B2 | 4/2021 | Valcarce et al. |
| 11,833,136 | B2 | 12/2023 | Freeman et al. |
| 11,974,989 | B2 | 5/2024 | Freeman et al. |
| 12,391,658 | B2 | 8/2025 | Diep et al. |
| 2002/0002190 | A1 | 1/2002 | Corbett et al. |
| 2002/0065239 | A1 | 5/2002 | Caplan et al. |
| 2002/0198200 | A1 | 12/2002 | Kester et al. |
| 2003/0171411 | A1 | 9/2003 | Kodra et al. |
| 2003/0220350 | A1 | 11/2003 | Lau et al. |
| 2004/0014789 | A1 | 1/2004 | Lau et al. |
| 2004/0014968 | A1 | 1/2004 | Bizzarro et al. |
| 2006/0246141 | A1 | 11/2006 | Liversidge et al. |
| 2006/0248141 | A1 | 11/2006 | Mukherjee |
| 2007/0054897 | A1 | 3/2007 | Murray et al. |
| 2008/0026987 | A1 | 1/2008 | Mackay et al. |
| 2008/0319028 | A1 | 12/2008 | Murray et al. |
| 2009/0105482 | A1 | 4/2009 | Lau et al. |
| 2009/0118501 | A1 | 5/2009 | Murray et al. |
| 2009/0216013 | A1 | 8/2009 | Murray et al. |
| 2009/0286800 | A1 | 11/2009 | Cheruvallath et al. |
| 2010/0028439 | A1 | 2/2010 | Jenkins et al. |
| 2010/0204288 | A1 | 8/2010 | Murray et al. |
| 2011/0245233 | A1 | 10/2011 | Anderson et al. |
| 2011/0301158 | A1 | 12/2011 | Polisetti et al. |
| 2011/0313007 | A1 | 12/2011 | Mjalli et al. |
| 2012/0071404 | A1 | 3/2012 | Tucker |
| 2014/0066372 | A1 | 3/2014 | Valcarce Lopez et al. |
| 2016/0015638 | A1 | 1/2016 | Mo et al. |
| 2016/0015816 | A1 | 1/2016 | Benjamin et al. |
| 2016/0184277 | A1 | 6/2016 | Mjalli et al. |
| 2018/0311314 | A1 | 11/2018 | Valcarce Lopez et al. |
| 2019/0046645 | A1 | 2/2019 | Benjamin et al. |
| 2019/0328713 | A1 | 10/2019 | Chen et al. |
| 2021/0169857 | A1 | 6/2021 | Freeman et al. |
| 2021/0169858 | A1 | 6/2021 | Freeman et al. |
| 2022/0233701 | A1 | 7/2022 | Benjamin et al. |
| 2023/0106983 | A1 | 4/2023 | Diep et al. |
| 2023/0219909 | A1 | 7/2023 | Teng et al. |
| 2024/0245656 | A1 | 7/2024 | Freeman et al. |
| 2025/0288681 | A1 | 9/2025 | Benjamin et al. |

FOREIGN PATENT DOCUMENTS

| | | | |
|---|---|---|---|
| CA | 2724116 | A1 | 11/2009 |
| EP | 0129408 | A2 | 12/1984 |
| EP | 0432040 | A1 | 6/1991 |
| EP | 0499299 | A2 | 8/1992 |
| EP | 0885890 | A1 | 12/1998 |
| EP | 0979823 | A1 | 2/2000 |
| EP | 1125922 | A1 | 8/2001 |
| EP | 1211246 | A1 | 6/2002 |
| EP | 2392575 | A1 | 12/2011 |
| GB | 771147 | A | 3/1957 |
| GB | 1185540 | A | 3/1970 |
| GB | 1195672 | A | 6/1970 |
| GB | 1260386 | A | 1/1972 |
| GB | 1282308 | A | 7/1972 |
| GB | 1318291 | A | 5/1973 |
| WO | WO-0017165 | A1 | 3/2000 |
| WO | WO-0026203 | A1 | 5/2000 |
| WO | WO-0045742 | A1 | 8/2000 |
| WO | WO-0053591 | A1 | 9/2000 |
| WO | WO-0058293 | A2 | 10/2000 |
| WO | WO-0100206 | A1 | 1/2001 |
| WO | WO-0144216 | A1 | 6/2001 |
| WO | WO-0144217 | A1 | 6/2001 |
| WO | WO-0157008 | A1 | 8/2001 |
| WO | WO-0183465 | A2 | 11/2001 |
| WO | WO-0183478 | A2 | 11/2001 |
| WO | WO-0185706 | A1 | 11/2001 |
| WO | WO-0185707 | A1 | 11/2001 |
| WO | WO-0208209 | A1 | 1/2002 |
| WO | WO-0214311 | A2 | 2/2002 |
| WO | WO-0246173 | A1 | 6/2002 |
| WO | WO-02070494 | A1 | 9/2002 |
| WO | WO-03055482 | A1 | 7/2003 |
| WO | WO-03070727 | A1 | 8/2003 |
| WO | WO-2004002481 | A1 | 1/2004 |
| WO | WO-2004085388 | A2 | 10/2004 |
| WO | WO-2005066145 | A1 | 7/2005 |
| WO | WO-2005086145 | A1 | 9/2005 |
| WO | WO-2005103050 | A2 | 11/2005 |
| WO | WO-2005123132 | A2 | 12/2005 |
| WO | WO-2007006760 | A1 | 1/2007 |
| WO | WO-2007006814 | A1 | 1/2007 |
| WO | WO-2008079787 | A2 | 7/2008 |
| WO | WO-2008084043 | A1 | 7/2008 |
| WO | WO-2008084044 | A1 | 7/2008 |
| WO | WO-2009129546 | A1 | 10/2009 |
| WO | WO-2009129548 | A1 | 10/2009 |
| WO | WO-2011149945 | A1 | 12/2011 |
| WO | WO-2013173417 | A2 | 11/2013 |
| WO | WO-2014137797 | A2 | 9/2014 |
| WO | WO-2014137799 | A1 | 9/2014 |
| WO | WO-2014176415 | A1 | 10/2014 |
| WO | WO-2019241089 | A1 | 12/2019 |
| WO | WO-2020068689 | A1 | 4/2020 |
| WO | WO-2021167840 | A1 | 8/2021 |
| WO | WO-2021252309 | A1 | 12/2021 |
| WO | WO-2021252311 | A1 | 12/2021 |

OTHER PUBLICATIONS

Bastin, Richard J. et al. Salt Selection and Optimisation Procedures for Pharmaceutical New Chemical Entities. Organic Process Research and Development 4(5):427-435 (2000).

Braga, Dario et al. Crystal polymorphism and multiple crystal forms. Structure and Bonding 132:25-50 (2009).

Caira, Mino R. Crystalline Polymorphism of Organic Compounds. In: Design of Organic Solids, Topics in Current Chemistry. Springer 198:163-208 (1998).

Donnelly, L.A. et al., Frequency and predictors of hypoglycaemia in Type 1 and insulin-treated Type 2 diabetes: a population-based study. Diabet Med 22(6):749-755 (2005).

Hilfiker, Rolf, et al. Relevance of Solid-State Properties for Pharmaceutical Products. In: Polymorphism: In the Pharmaceutical Industry. Wiley:1-19 (2006).

Kumar, Challa V, and Anita Chaudhari. Proteins Immobilized at the Galleries of Layered a-Zirconium Phosphate: Structure and Activity Studies. Journal of the American Chemical Society 122(5):830-837 (2000).

Terada, Katsuhide. Application of Thermal Analysis to the Pharmaceutical Development. Netsu Sokutei 38(2):46-53 (2010).

Yamano, Mitsuhisa. Approach to Crystal Polymorph in Process Research of New Drug. Journal of Synthetic Organic Chemistry Japan 65(9):907-913 (2007).

(56) References Cited

OTHER PUBLICATIONS

Yoshinori, Nakai, and Manabu Hanano. New Pharmaceutical Science. Nanzando Co., Ltd:1-26 (1984).
Bhattacharya et al. Chapter 9: Thermoanalytical and Crystallographic Methods. Polymorphism in pharmaceutical solids. pp. 318-346 (2018).
Brittain. Polymorphism and Solvatomorphism J Pharm Sci 98(5):1617-1642 (2009).
Gabriely et al. Fructose normalizes specific counterregulatory responses to hypoglycemia in patients with type 1 diabetes. Diabetes 54(3):609-616 (2005).
Morisette et al. High-throughput crystallization: polymorphs, slats, co-crystals, and solvates of pharmaceutical solids. Advanced Drug Delivery Reviews 56:275-300 (2004).
Morral et al. Adenovirus-mediated expression of glucokinase in the liver as an adjuvant treatment for type 1 diabetes. Hum Gene Ther 12(13):1561-1570 (2002).
Agiostratidou et al., Standardizing Clinically Meaningful Outcome Measures Beyond HbA1c for Type 1 Diabetes: A Consensus Report of the American Association of Clinical Endocrinologists, the American Association of Diabetes Educators, the American Diabetes Association, the Endocrine Society, JDRF International, The Leona M. and Harry B. Helmsley Charitable Trust, the Pediatric Endocrine Society, and the T1D Exchange. Diabetes Care 40:1622-1630 (2017).
Agius et al. Regulation of glycogen synthesis from glucose and gluconeogenic precursors by insulin in periportal and perivenous rat hepatocytes. Biochem J. 266:91-102 (1990).
Aicher et al. ARRY-403, A Novel Glucokinase Activator with Potent Glucose-Dependent AntiHyperglycemic Activity in Animal Models of Type 2 Diabetes Mellitus. Poster 126—Keystone Symposium: Type 2 Diabetes and Insulin Resistance (J3), Jan. 20-25, 2009, Banff, AB (Array Biopharma).
Battelino et al. Clinical Targets for Continuous Glucose Monitoring Data. Diabetes Care 42:1593-1603 (2019).
Berge et al. Pharmaceutical Salts. Journal of Pharmaceutical Sciences 66(1):1-19 (Jan. 1977).
Bonadonna et al. Piragliatin (RO4389620), a Novel Glucokinase Activator, Lowers Plasma Glucose Both in the Postabsorptive State and after a Glucose Challenge in Patients with Type 2 Diabetes Mellitus: A Mechanistic Study. J Clin Endocrinol Metab, 95(11):1-9 (2010).
Buse et al. Simplici-T1 First Clinical Trial to Test Activation of Glucokinase as an Adjunctive Treatment for Type 1 Diabetes. Diabetes 67 (Supplement_1): 126-LB (Abstract) (Mar. 2018).
Buse et al. Simplici-T1: First Clinical Trial to Test Activation of Glucokinase as an Adjunctive Treatment for Type 1 Diabetes Poster presented at the 78th Scientific Session of ADA in Orlando, FL, Jun. 22-26, 2018.
Buse et al. The Simplici-TI Trial: Glucokinase activator (GKA) TTP399 improves glycemic control in patients with type 1 diabetes (T1D) Poster presented at the 80th Scientific Session of ADA, Jun. 12-16, 2020.
Castelhano et al., Glucokinase-activating ureas. Bioorg Med Chem Lett 15:1501-1504 (2005).
Chipkin et al., Joslin's Diabetes, pp. 97-115 (1994).
ClinicalTrials.gov—Clinical Trials Identifier NCT01247363 (2011).
Colowick., The Hexokinases. The Enzymes 9:1-48 (1973).
Drucker et al. Sitagliptin.Nat Rev Drug Discov 6:109-110 (2007).
Eiki et al. Pharmacokinetic and Pharmacodynamic Properties of the Glucokinase Activator MK-0941 in Rodent Models of Type 2 Diabetes and Healthy Dogs. Mol Pharmacol 80:1156-1165 (2011).
Ericsson et al. The glucokinase activator AZD6370 decreases fasting and postprandial glucose in type 2 diabetes mellitus patients with effects influenced by dosing regimen and food. Diabetes Research and Clinical Practice 98:436-444 (2012).
Evans et al., Design of potent, orally effective, nonpeptidal antagonists of the peptide hormone cholecystokinin. PNAS USA 83(13):4918-4922 (1986 ).
Ferre et al., Evidence from transgenic mice that glucokinase is rate limiting for glucose utilization in the liver. The Faseb Journal 10:1213-1218 (1996).
Freeman et al. Mechanism matters: preliminary evidence that activation of glucokinase by TTP399 does not increase plasma or urine ketones in type 1 diabetes, P51, presented at the 56th European Association for the Study of Diabetes Conference—Virtual, Sep. 22, 2020.
Gardner., Studies In The Polyoxyphenol Series: Iii. Syntheses Of Substituted Phenylureas From Methylated And Ethylated Vanillin. Canadian Journal Research 26:681-693 (1948).
Garg et al. Effects of Sotagliflozin Added to Insulin in Patients with Type 1 Diabetes. N Engl J Med 377:2337-48 (2017).
Girard et al., Mechanisms by which carbohydrates regulate expression of genes for glycolytic and lipogenic enzymes. Annu Rev Nutr 17:325-352 (1997).
Glaser et al., Familial hyperinsulinism caused by an activating glucokinase mutation. N Engl J Med 338:226-230 (1998).
Guidance for Industry, Estimating the Maximum Safe Starting Does in Initial Clinical Trials for Therapeutics in Adult Healthy Volunteers, FDA. Jul. 2005 activity in animal modest of type 2 diabetes mellitus. Diabetologia 52(Suppl):S342 (2009).
Heitmeier et al., Hydroxyphenethylamino Derivatives Of Various Nitrogen Heterocycles. J Med Chem 7(3):288-293 (1964).
Hinklin et al. ARRY-403, a glucokinase activator with potent glucose-dependent anti-hyperglycaemic activity in animal models of type 2 diabetes mellitus. Diabetologia 52(Supp):S342 (2009).
Johnson et al. Glucose-dependent modulation of insulin secretion and intracellular calcium ions by GKA50, a glucokinase activator. Diabetes 56:1694-1702 (2007).
Kos et al., New treatments for type 2 diabetes. J.R.Coll. Physicians Edinb. 39(3):227-230 (2009).
Li et al. The Effect of the Physical States of Binders on High-Shear Wet Granulation and Granule Prop-erties: A Mechanistic Approach Toward Understanding High-Shear Wet Granulation Process. Part II. Granulation and Granule Properties. J Pharm Sci 100:294-310 (2011).
Liang et al., Variable effects of maturity-onset-diabetes-of-youth (MODY)-associated glucokinase mutations on substrate interactions and stability of the enzyme. Biochem Journal 309:167-173 (1995).
Lin et al. Development of potential novel cushioning agents for the compaction of coated multi-particulates by co-processing micronized lactose with polymers. Eur J Pharm Biopharm 79(2):406-179:406-415 (2011).
Lindstrom. The Physiology of Obese-Hyperglycemic Mice [ob/ob Mice] Scientific World Journal 7:666-685 (2007).
Lu et al. Characterization of a Novel Glucokinase Activator in Rat and Mouse Models. PLoS One 9(2):88431 (2014).
Mann. The Influence of Obesity on Health. N Engl J Med 291:226-232 (1974).
Mathieu et al. Glucose Variable In Type 1 Diabetes Studies With Dapagliflozin: Pooled Analysis Of Continuous Glucose Monitoring Data From DEPICT-1 and 2, Diabetes Care 42:1081-1087 and supplementary data (2019).
Matschinsky et al. Glucokinase activators for diabetes therapy: May 2010 status report. Diabetes Care 34(Suppl 2):S236-S243 (2011).
Matschinsky et al. Research and Development of Glucokinase Activators for Diabetes Therapy: Theoretical and Practical Aspects. Handb Exp Pharmacol 203:357-401 (2011).
Matschinsky. GKAs for diabetes therapy: why no clinically useful drug after two decades of trying? Trends Pharmacol Sci 34(2):90-9 (2013).
Mccarty. In type 1 diabetics, high-dose biotin may compensate for low hepatic insulin exposure, promoting a more normal expression of glycolytic and gluconeogenic enzymes and thereby aiding glycemic control. Medical Hypotheses 95:45-8 (2016).
Mcvean et al., Combination Therapy of ARRY-403 with Metformin. Sitagliptin or Pioglitazone Results in Additive Glucose Lowering In Female ZDF Rats, Poster 104—Keystone Symposium! Type 2 Diabetes and Insulin Resistance (J3), Jan. 20-25, 2009, Banff, AB (Array Biopharma).

(56) References Cited

OTHER PUBLICATIONS

Meglasson et al., New perspectives on pancreatic islet glucokinase. Am J Physiol 246:E1-E13 (1984).
Migoya et al. The Glucokinase (GK) Activator MK-0599 Lowers Plasma Glucose Concentrations in Healthy Non-Diabetic Subjects. Diabetologia 52:S344-S344 Abstract (2009).
Mylari et al., Design And Synthesis Of A Novel Family Of Triazine-Based Inhibitors Of Sorbitol Dehydrogenase With Oral Activity: 1-{4-[3r,5s-Dimethyl-4-(4-Methyl-[1,3,5]Triazin-2-Yl)-Piperazin-1-Yl]-[1,3,5]Triazin-2-Yl)--(R) Ethanol. Bioorgan Med Chem 11:4179-4188 (2003).
Nakamura et al. Control of beta cell function and proliferation in mice stimulated by small-molecule glucokinase activator under various conditions. Diabetologia 55(5):1745-1754 (2012).
Nathan et al. Medical Management of Hyperglycemia in Type 2 Diabetes: A Consensus Algorithm for the Initiation and Adjustment of Therapy. Diabetes Care 32:193-203 (2009).
Newton. Chapter 12: Drug Release from Capsules. Phamaceutical Capsules, Pharmaceutical Press, Podczeck et al. Eds. 2nd Ed. (pp. 213-237) (2004).
Pal et al. Recent advances in glucokinase activators for the treatment of type 2 diabetes. Drug Discovery Today 14(15/16):784-792 (2009).
Patani et al. Bioisosterism: A Rational Approach in Drug Design. Chem. Rev. 96:3147-3176 (1996).
PCT/US2021/017743 International Search Report and Written Opinion dated Apr. 21, 2021.
PCT/US2021/036082 International Search Report and Written Opinion dated Sep. 8, 2021.
PCT/US2021/036084 International Search Report and Written Opinion dated Sep. 9, 2021.
Pfefferkom. Strategies for the design of hepaloselective glucokinase activators to treat type 2 diabetes. Expert Opin. Drug Discov. 8(3):319-330 (2013).
Pfuetzner et al. Intensive insulin therapy with insulin lispro in patients with type 1 diabetes reduces the frequency of hypoglycemic episodes. Exp Clin Endocrinol Diabetes 104(1):25-30 (abstract) (1996).
Polakof. Diabetes Therapy: Novel Patents Targeting the Glucose-Induced Insulin Secretion. Recent Pat DNA Gene Seq 4(1):1-9 (2010).
Printz et al. Mammalian glucokinase. Ann Rev Nutr 13:463-496 (1993).
Priyadarsini et al. Glucokinase Activators: A Glucose Sensor Role In Pancreatic Islets And Hepatocyte. International Journal of Pharmacy and Pharmaceutical Sciences 4(2):81-87 (2012).
Purchase et al., Tetrazole-Substituted Ureas As Inhibitors Of Acyl-Coa:Cholesterol O-Acyltransferase (Acat) A Novel Preparation Of Ureas From Weakly Nucleophilic Amines. Biorgan Med Chem Lett 6(15):1753-1758 (1996).
Ripsin et al., Management of Blood Glucose in Type 2 Diabetes Mellitus. American Family Physician 79:29-36 (Jan. 2009).
Rosenstock et al. Empagliflozin As Adjunctive To Insulin Therapy In Type 1 Diabetes: The EASE Trials. Diabetes Care 41:2560-9 (2018).
Sands et al. Sotagliflozin, a Dual SGLT1 and SGLT2 Inhibitor, as Adjunct Therapy to Insulin in Type 1 Diabetes. Diabetes Care 38(7):1181-1188 (2015).
Sands et al. Sotagliflozin, a Dual SGLT1 and SGLT2 Inhibitor, as Adjunct Therapy to Insulin in Type 1 Diabetes. Diabetes Care 38(7):1181-1188 (Supplementary Data) (2015).
Valcarce, C., et al., The Simplici-T1 trial: Activation of glucokinase by TTP399 improves glycemic control in patients with T1DM, P50, presented at the 56th European Association for the Study of Diabetes Conference—Virtual, Sep. 22, 2020.
Valcarce et al. TTP399, A Liver Selective Glucokinase Activator Increases Efficacy of Currently Marketed Therapies for Type 2 Diabetes. Jun. 2015. ADA 75th Scientific Sessions, Boston (Abstract 1271-P).
Valcarce et al. TTP399, a Liver-Selective Glucose Kinase Activator (GKA), Lowers Glucose and Does Not Increase Lipids in Subjects with Type 2 Diabetes Mellitus (T2DM). Jun. 2014. ADA 74th Scientific Sessions. (Abstract 122-OR).
Valcarce et al. Results from the sentinel and learning phase of the Simplici-T1 study, thefirst clinical trial to test activation of glucokinase as an adjunctive treatment for type 1 diabetes. Presented at the 55th EASD conference, Sep. 18, 2019, Barcelona, Spain.
Valcarce et al. The Simplici-T1 Trial: Relationship Between Glycemic Control and Insulin Dose Poster presented at the 80th Scientific Session of ADA, Jun. 12-16, 2020.
Valcarce et al. TTP399, A Liver Selective Glucokinase Activator (GKA) the Preserves the Physiological Regulation of Glucokinase (GK) by GK Regulatory Protein (GKRP). Jun. 2015. ADA 75th Scientific Sessions, Boston (Poster 1168-P).
Valcarce et al. TTP399, A Liver Selective Glucokinase Activator (GKA) the Preserves the Physiological Regulation of Glucokinase (GK) by OK Regulatory Protein (GKRP). Jun. 2015. ADA 75th Scientific Sessions. Boston (Abstract 1168-P).
Valcarce et al. TTP399. A Liver Selective Glucokinase Activator Increases Efficacy of Currently Marketed Therapies for Type 2 Diabetes. Jun. 2015. ADA 75th Scientific Sessions: Boston (Poster 1271-P).
Valcarce et al. TTP399, a Liver-Selective Glucose Kinase Activator (GKA), Lowers Glucose and Does Not Increase Lipids in Subjects with Type 2 Diabetes Mellitus (T2DM). Jun. 2014. ADA 74th Scientific Sessions. (Power Point 122-OR).
Valcarce et al. TTP399, a Novel, Liver Selective Glucokinase Activator: Results from a 10 day Pilot Study in Patients with type 2 Diabetes Mellitus *(T2DM) Naive to Drug, Poster presented at the 76th Scientific Sessions of the American Diabetes Association in New Orleans, LA, Jun. 11-13, 2016.
Valcarce. Selective Activation of Glucokinase (GK) in the Liver: Improves Glycemic Control and Reduces Insulin Need as Well as Risk of Ketoacidosis in Type 1 Diabetic Minipigs, presented at the Keystone Symposia on Diabetes, Jan. 22-26, 2017, Keystone, Colorado.
Valcarce. The Importance of Tissue Selectivity and Preservation of the Physiological Regulation when Targeting Key Metabolic Regulators as Glucokinase, Poster presented at the Keystone Conference in La Jolla, CA, Apr. 17-20, 2016.
Vella et al. Abstract TTP399: A liver-selective and Therapeutically Viable Glucokinase Activator . . . Study presented at the 17th Annual Rachmiel Levine-Arthur Riggs Diabetes Research Symposium, Endocrine Society ENDO2017 Conference, Orlando, Florida, Mar. 27-Apr. 4, 2017.
Vella et al. Targeting hepatic glucokinase to treat diabetes with TTP399, a hepatoselective glucokinase activator. Sci Transl Med. 11(475):eaau3441 (2019).
Vella et al., TTP399: A liver-selective and Therapeutically Viable Glucokinase Activator. Results from a 6-Month Phase 2 Study presented at the 17th Annual Rachmiel Levine-Arthur Riggs Diabetes Research Symposium, Endocrine Society ENDO2017 Conference, Orlando, Florida, Mar. 27-Apr. 4, 2017.
Brittain, H.G., et al. Polymorphism in Pharmaceutical Solids. Marcel Dekker, Inc., 192(1-10):183-226 (1999).
Yu, Lian et al. Physical characterization of polymorphic drugs: an integrated characterization strategy. PSTT 1(3):118-127 (1998).
Co-pending U.S. Appl. No. 19/271,551, inventors Diep; Nhut et al., filed Jul. 16, 2025.
Gao, Bowei et al. Multi-component non-fullerene acceptors with tunable bandgap structures for efficient organic solar cells. Journal of Materials Chemistry 6(46):23644-23649 (2018).
Meininger, Gary E et al. Effects of MK-0941, a novel glucokinase activator, on glycemic control in insulin-treated patients with type 2 diabetes. Diabetes Care 34(12):2560-2566 (2011).
Sareen, Swati et al. Improvement in solubility of poor water-soluble drugs by solid dispersion. Int J Pharm Investig 2(1): 12-7 (2012).
Sikarra, Deepshikha et al. Techniques for solubility enhancement of poorly soluble drugs: an overview. JMPAS 1:1-22 (2012).

CRYSTALLINE FORMS OF {2-[3-CYCLOHEXYL-3-(TRANS-4-PROPOXY-CYCLOHEXYL)-UREIDO]-THIAZOL-5-YLSULFANYL}-ACETIC ACID AND USES THEREOF

FIELD OF THE INVENTION

The present disclosure relates to a) crystalline forms of {2-[3-cyclohexyl-3-(trans-4-propoxy-cyclohexyl)-ureido]-thiazol-5-ylsulfanyl}-acetic acid ("Compound I" or "API"); b) pharmaceutical compositions, comprising one or more crystalline forms of {2-[3-cyclohexyl-3-(trans-4-propoxy-cyclohexyl)-ureido]-thiazol-5-ylsulfanyl}-acetic acid, and optionally, a pharmaceutically acceptable carrier; and c) methods of treating a type of diabetes mellitus and other disorders by administering one or more crystalline forms of {2-[3-cyclohexyl-3-(trans-4-propoxy-cyclohexyl)-ureido]-thiazol-5-ylsulfanyl}-acetic acid to a subject in need thereof.

BACKGROUND

Glucokinase ("GK") is a key regulator of glucose homeostasis and acts as the physiological glucose sensor, changing its conformation, activity, and/or intracellular location in parallel with changes in glucose concentrations. GK has two main distinctive characteristics that make it a good choice for blood glucose control. First, its expression is mostly limited to tissues that require glucose-sensing (mainly liver and pancreatic β-cells). Second, GK is able to sense changes in serum glucose levels and modulate changes in liver glucose metabolism that in turn regulate the balance between hepatic glucose production (HGP) and glucose consumption, and to modulate changes in insulin secretion by the beta-cells. The concept of GK activation for the treatment of diabetes is attractive because it has proven to be effective and safe in normalizing glycemia in animal models of type 1 and type 2 diabetes by a mechanism entirely distinct from the action of antidiabetic therapies currently on the market.

Although multiple small-molecule activators of GK have been in clinical development, their initial therapeutic promise has been hampered by the occurrence of hypoglycemia, increased triglycerides (TG) concentrations, and loss of efficacy over time. These adverse events (AEs) were related to ongoing β cell activation. Compound I, a hepatoselective agent, does not cause similar adversarial effects. (Vella et al., Science Translational Medicine 16 Jan. 2019).

Compound I is an oral, small molecule, liver selective glucokinase activator that improves glycemic control and may not induce hypoglycemia, dyslipidemia, or pathological increases of glycogen and TG in the liver at therapeutically relevant doses. (Vella et al., Science Translational Medicine 16 Jan. 2019).

Not all compounds that are GK activators have characteristics affording the best potential to become useful therapeutics. Some of these characteristics include high affinity at the glucokinase, duration of glucokinase activation, oral bioavailability, tissue distribution, and stability (e.g., ability to formulate or crystallize, shelf life). Favorable characteristics can lead to improved safety, tolerability, efficacy, therapeutic index, patient compliance, cost efficiency, manufacturing ease, etc.

In addition, the isolation and commercial-scale preparation of a crystalline form of Compound I and corresponding pharmaceutical formulations having acceptable solid state properties (including chemical stability, thermal stability, solubility, hygroscopicity, and/or particle size), compound manufacturability (including yield, impurity rejection during crystallization, filtration properties, drying properties, and milling properties), and formulation feasibility (including stability with respect to pressure or compression forces during tableting) present a number of challenges.

Accordingly, there is a current need for one or more crystalline forms of Compound I that have an acceptable balance of these properties and can be used in the preparation of pharmaceutically acceptable solid dosage forms.

BRIEF SUMMARY OF THE INVENTION

In one aspect, the present disclosure relates to a crystalline form of {2-[3-cyclohexyl-3-(trans-4-propoxy-cyclohexyl)-ureido]-thiazol-5-ylsulfanyl}-acetic acid. In one aspect, the crystalline form is anhydrous. In another aspect, the crystalline form is solvated.

In one aspect, the present disclosure relates to crystalline form of {2-[3-cyclohexyl-3-(trans-4-propoxy-cyclohexyl)-ureido]-thiazol-5-ylsulfanyl}-acetic acid of Formula (I)

(I)

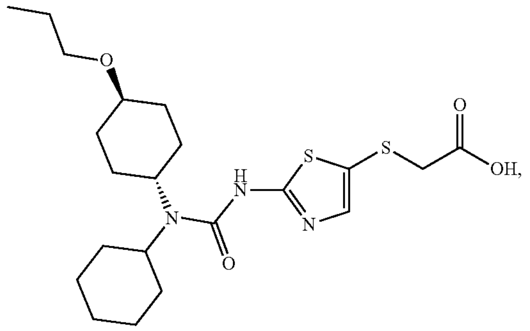

selected from the group consisting of:

a) a crystalline form characterized by an XRPD pattern having peaks at 16.9±0.2, 17.4±0.2, and 20.1±0.2 degrees two theta;
b) a crystalline form characterized by an XRPD pattern having peaks at 11.0±0.2, 11.6±0.2, and 17.8±0.2 degrees two theta;
c) a crystalline form characterized by an XRPD pattern having peaks at 4.3±0.2, 17.4±0.2, and 21.6±0.2 degrees two theta;
d) a crystalline form characterized by an XRPD pattern having peaks at 5.3±0.2, 8.7±0.2, and 26.4±0.2 degrees two theta;
e) a crystalline form characterized by an XRPD pattern having peaks at 5.8±0.2, 17.9±0.2, and 18.9±0.2 degrees two theta;
f) a crystalline form characterized by an XRPD pattern having peaks at 3.8±0.2, 9.5±0.2, and 16.8±0.2 degrees two theta;
g) a crystalline form characterized by an XRPD pattern having peaks at 3.4±0.2, 21.2±0.2, and 21.9±0.2 degrees two theta;
h) a crystalline form characterized by an XRPD pattern having peaks at 3.8±0.2, 5.3±0.2, and 8.5±0.2 degrees two theta;
i) a crystalline form characterized by an XRPD pattern having peaks at 5.0±0.2, 16.8±0.2, and 18.8±0.2 degrees two theta; and
j) a crystalline form characterized by an XRPD pattern having peaks at 5.9±0.2, 17.4±0.2, and 18.8±0.2 degrees two theta.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 16.9±0.2, 17.4±0.2, and 20.1±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is characterized by an endothermic peak with onset at about 160° C., as determined by DSC.

In one aspect, the crystalline form of {2-[3-cyclohexyl-3-(trans-4-propoxy-cyclohexyl)-ureido]-thiazol-5-ylsulfanyl}-acetic acid is characterized by an IR pattern having peaks at 1099.7±2.0, 1158.0±2.0, and 1313.2±2.0 $cm^{-1}$.

In one aspect, the crystalline form of {2-[3-cyclohexyl-3-(trans-4-propoxy-cyclohexyl)-ureido]-thiazol-5-ylsulfanyl}-acetic acid is characterized by a $^{13}C$ solid state NMR substantially as shown in FIG. 4.

In one aspect, the crystalline form of {2-[3-cyclohexyl-3-(trans-4-propoxy-cyclohexyl)-ureido]-thiazol-5-ylsulfanyl}-acetic acid has a unit cell that indexes as primitive monoclinic. In another aspect, the crystalline form of {2-[3-cyclohexyl-3-(trans-4-propoxy-cyclohexyl)-ureido]-thiazol-5-ylsulfanyl}-acetic acid has a unit cell with an a value of about 10.193 Å, a b value of about 12.256 Å, and a c value of about 18.991 Å. In another aspect, the crystalline form of {2-[3-cyclohexyl-3-(trans-4-propoxy-cyclohexyl)-ureido]-thiazol-5-ylsulfanyl}-acetic acid has a unit cell with a volume of about 2370.9 $Å^3$.

In one aspect, the crystalline form of {2-[3-cyclohexyl-3-(trans-4-propoxy-cyclohexyl)-ureido]-thiazol-5-ylsulfanyl}-acetic acid is Form A.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 11.0±0.2, 11.6±0.2, and 17.8±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is characterized by an endothermic peak with onset at about 166° C., as determined by DSC.

In one aspect, the crystalline form of {2-[3-cyclohexyl-3-(trans-4-propoxy-cyclohexyl)-ureido]-thiazol-5-ylsulfanyl}-acetic acid is characterized by an IR pattern having peaks at 1310.1±2.0, 1514.4±2.0, and 1661.3±2.0 $cm^{-1}$.

In one aspect, the crystalline form of of {2-[3-cyclohexyl-3-(trans-4-propoxy-cyclohexyl)-ureido]-thiazol-5-ylsulfanyl}-acetic acid is characterized by a $^{13}C$ solid state NMR substantially as shown in FIG. 8.

In one aspect, the crystalline form of {2-[3-cyclohexyl-3-(trans-4-propoxy-cyclohexyl)-ureido]-thiazol-5-ylsulfanyl}-acetic acid has a unit cell that indexes as primitive monoclinic. In another aspect, the crystalline form of {2-[3-cyclohexyl-3-(trans-4-propoxy-cyclohexyl)-ureido]-thiazol-5-ylsulfanyl}-acetic acid has a unit cell with an a value of about 11.028 Å, a b value of about 11.933 Å, and a c value of about 18.737 Å. In another aspect, the crystalline form of {2-[3-cyclohexyl-3-(trans-4-propoxy-cyclohexyl)-ureido]-thiazol-5-ylsulfanyl}-acetic acid has a unit cell with a volume of about 2449.0 $Å^3$.

In one aspect, the crystalline form of {2-[3-cyclohexyl-3-(trans-4-propoxy-cyclohexyl)-ureido]-thiazol-5-ylsulfanyl}-acetic acid is Form B.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 4.3±0.2, 17.4±0.2, and 21.6±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is characterized by an endothermic peak with onset at about 149° C., as determined by DSC.

In one aspect, the crystalline form of {2-[3-cyclohexyl-3-(trans-4-propoxy-cyclohexyl)-ureido]-thiazol-5-ylsulfanyl}-acetic acid is a dichloromethane solvate.

In one aspect, the crystalline form of {2-[3-cyclohexyl-3-(trans-4-propoxy-cyclohexyl)-ureido]-thiazol-5-ylsulfanyl}-acetic acid has a unit cell that indexes as primitive monoclinic. In another aspect, the crystalline form of {2-[3-cyclohexyl-3-(trans-4-propoxy-cyclohexyl)-ureido]-thiazol-5-ylsulfanyl}-acetic acid has a unit cell with an a value of about 5.541 Å, a b value of about 13.040 Å, and a c value of about 40.818 Å. In another aspect, the crystalline form of {2-[3-cyclohexyl-3-(trans-4-propoxy-cyclohexyl)-ureido]-thiazol-5-ylsulfanyl}-acetic acid has a unit cell with a volume of about 2947.6 $Å^3$.

In one aspect, the crystalline form of {2-[3-cyclohexyl-3-(trans-4-propoxy-cyclohexyl)-ureido]-thiazol-5-ylsulfanyl}-acetic acid is Form C.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 5.3±0.2, 8.7±0.2, and 26.4±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is characterized by an endothermic peak with onset at about 147° C., as determined by DSC.

In one aspect, the crystalline form of of {2-[3-cyclohexyl-3-(trans-4-propoxy-cyclohexyl)-ureido]-thiazol-5-ylsulfanyl}-acetic acid is characterized by a $^{13}C$ solid state NMR substantially as shown in FIG. 13.

In one aspect, the crystalline form of {2-[3-cyclohexyl-3-(trans-4-propoxy-cyclohexyl)-ureido]-thiazol-5-ylsulfanyl}-acetic acid is Form D.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 5.8±0.2, 17.9±0.2, and 18.9±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is characterized by an endothermic peak with onset at about 171° C., as determined by DSC.

In one aspect, the crystalline form of {2-[3-cyclohexyl-3-(trans-4-propoxy-cyclohexyl)-ureido]-thiazol-5-ylsulfanyl}-acetic acid is Form E.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 3.8±0.2, 9.5±0.2, and 16.8±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is Form F.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 3.4±0.2, 21.2±0.2, and 21.9±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is Form G.

In one aspect, the present disclosure relates to a crystalline form of {2-[3-cyclohexyl-3-(trans-4-propoxy-cyclohexyl)- ureido]-thiazol-5-ylsulfanyl}-acetic acid, characterized by an XRPD pattern having peaks at 3.8±0.2, 5.3±0.2, and 8.5±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is Form H.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 5.0±0.2, 16.8±0.2, and 18.8±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is Form I.

In one aspect, the present disclosure relates to a crystalline form of {2-[3-cyclohexyl-3-(trans-4-propoxy-cyclohexyl)-ureido]-thiazol-5-ylsulfanyl}-acetic acid, characterized by an XRPD pattern having peaks at 5.9±0.2, 17.4±0.2, and 18.8±0.2 degrees two theta.

In one aspect, the crystalline form of {2-[3-cyclohexyl-3-(trans-4-propoxy-cyclohexyl)-ureido]-thiazol-5-ylsulfanyl}-acetic acid is characterized by an endothermic peak with onset at about 164° C., as determined by DSC.

In one aspect, the crystalline form of {2-[3-cyclohexyl-3-(trans-4-propoxy-cyclohexyl)-ureido]-thiazol-5-ylsulfanyl}-acetic acid is Form J.

In some aspects, the crystalline form is substantially free of other polymorphic forms. In some aspects, the crystalline form has a polymorphic purity of at least about 80%.

In one aspect, the crystalline form of {2-[3-cyclohexyl-3-(trans-4-propoxy-cyclohexyl)-ureido]-thiazol-5-ylsulfanyl}-acetic acid is selected from the group consisting of Form A, Form B, Form C, Form D, Form E, Form F, Form G, Form H, Form I, and Form J. In one aspect, the crystalline form of {2-[3-cyclohexyl-3-(trans-4-propoxy-cyclohexyl)-ureido]-thiazol-5-ylsulfanyl}-acetic acid is Form A.

In some aspects, the present disclosure relates to a pharmaceutical composition comprising any one or more of the crystalline forms discussed above and a pharmaceutically acceptable carrier, diluent, excipient, or a mixture thereof.

In some aspects, the present disclosure relates to a method of treating a type of diabetes mellitus or other disorders, where the method comprises administering the pharmaceutical composition discussed above to a patient in need thereof. In some aspects, the type of diabetes mellitus is type 1 diabetes. In some aspects, the type of diabetes mellitus is type 2 diabetes.

In some aspects, the pharmaceutical composition is administered orally. In some aspects, the pharmaceutical composition is administered as a tablet. In some aspects, the patient is administered up to about 2000 mg of {2-[3-cyclohexyl-3-(trans-4-propoxy-cyclohexyl)-ureido]-thiazol-5-ylsulfanyl}-acetic acid daily.

In some aspects, the present disclosure provides methods of making a crystalline form of {2-[3-cyclohexyl-3-(trans-4-propoxy-cyclohexyl)-ureido]-thiazol-5-ylsulfanyl}-acetic acid where the crystalline form is selected from the group consisting of Form A, Form B, Form C, Form D, Form E, Form F, Form G, Form H, Form I, and Form J.

DETAILED DESCRIPTION OF THE INVENTION

I. Definitions

Figure 1:
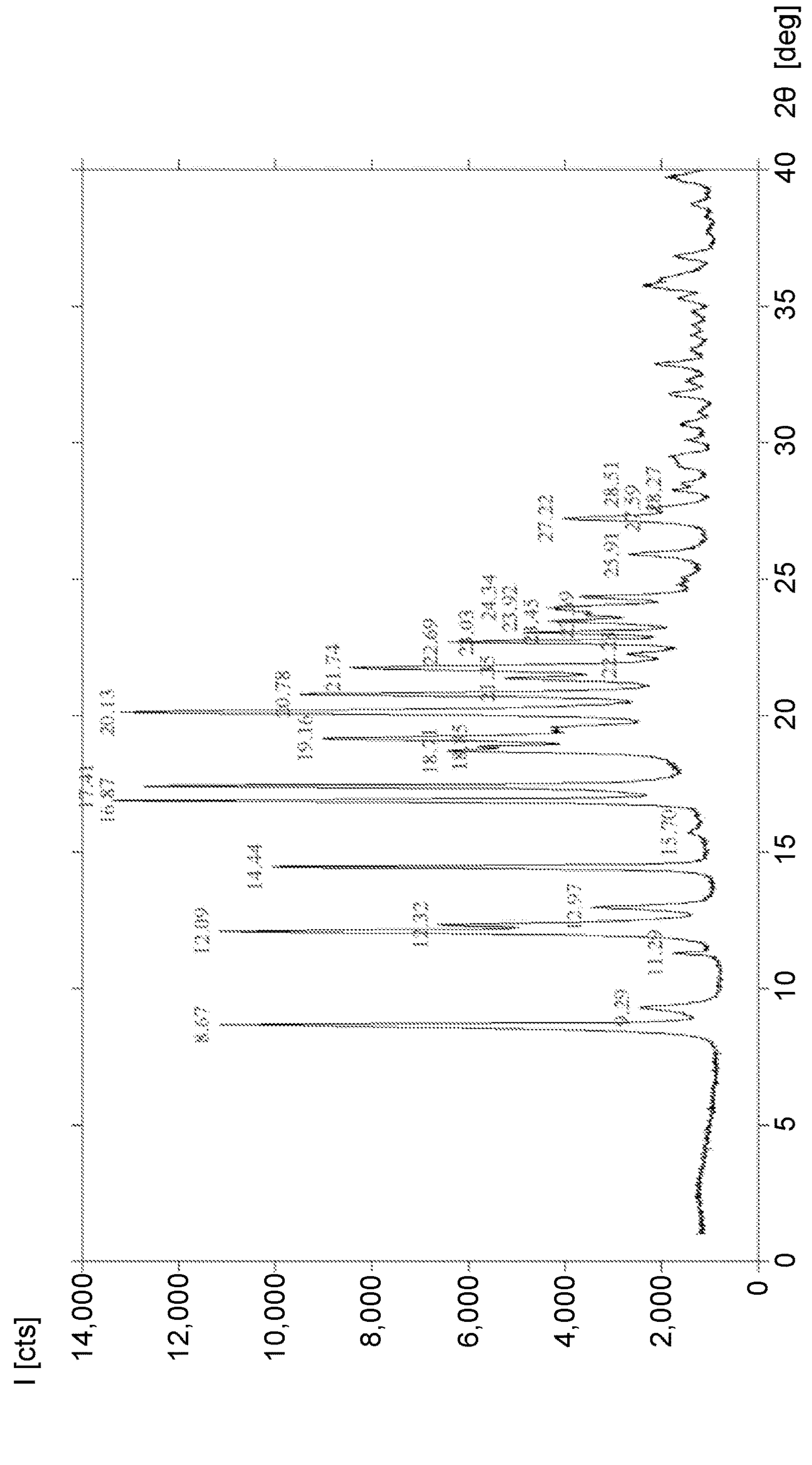
FIG. 1 is a powder X-ray diffraction pattern ("XRPD") corresponding to crystalline Form A.

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "Compound I" refers to the chemical compound {2-[3-cyclohexyl-3-(trans-4-propoxy-cyclohexyl)-ureido]-thiazol-5-ylsulfanyl}-acetic acid.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating the cause(s) of the disorder, disease, or condition itself.

The terms "pharmaceutically acceptable carrier," "pharmaceutically acceptable diluent," or "pharmaceutically acceptable excipient," refer to a pharmaceutically-acceptable material, composition, or vehicle, such as a liquid or solid filler, diluent, excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy,* 21st Edition, Lippincott Williams & Wilkins: Philadelphia, PA, 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; Pharmaceutical Preformulation and Formulation, Gibson Ed., CRC Press LLC: Boca Raton, FL, 2004 (incorporated herein by reference).

The terms "about" or "approximately" means an acceptable error for a particular value as determined by one of ordinary skill in the art, which depends in part on how the value is measured or determined. In certain aspects, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, delaying onset of, or ameliorating one or more symptoms of a condition, disorder, or disease. As used herein, "active ingredient" and "active substance" may be an optically active isomer of a compound described herein.

The term "solvate" or "solvated" refers to a compound provided herein or a salt thereof, which further includes a stoichiometric or non-stoichiometric amount of solvent bound by non-covalent intermolecular forces. Where the solvent is water, the solvate is a hydrate. Where the solvent includes ethanol, the compound can be an ethanol solvate.

The term "polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences,* $18^{th}$ ed., Mack Publishing, Easton PA, 173 (1990); *The United States Pharmacopeia,* $23^{rd}$ ed., 1843-1844 (1995) (incorporated herein by reference).

Crystalline forms are most commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

The term "anhydrate" or "anhydrous" as applied to a compound refers to a solid state wherein the compound contains no structural water within the crystal lattice.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

For all embodiments disclosed herein, a peak positional reproducibility is associated with the values of degree-2θ (XRPD), ppm ($^{13}C$ solid state NMR), and $cm^{-1}$ (IR). Accordingly, it will be understood that all peaks disclosed herein have the value disclosed ±the peak positional reproducibility associated with each analytical technique. The XRPD peak positional reproducibility is ±0.2 expressed in degree-2θ. The $^{13}C$ NMR peak positional reproducibility is +0.2 ppm. The IR peak positional reproducibility is ±2 $cm^{-1}$.

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

II. Crystalline Forms

In one aspect, the present disclosure relates to a crystalline form of {2-[3-cyclohexyl-3-(trans-4-propoxy-cyclohexyl)-ureido]-thiazol-5-ylsulfanyl}-acetic acid. In one aspect, the crystalline form is anhydrous as determined by $^{1}H$ NMR. In another aspect, the crystalline form is solvated as determined by $^{1}H$ NMR.

In one aspect, the present disclosure relates to crystalline form of {2-[3-cyclohexyl-3-(trans-4-propoxy-cyclohexyl)-ureido]-thiazol-5-ylsulfanyl}-acetic acid of Formula (I)

(I)

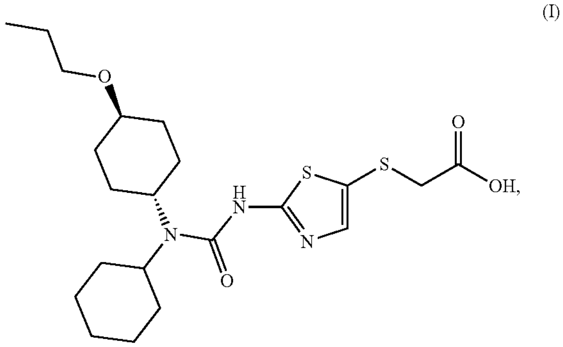 [SMILES: CCCO[C@H]1CC[C@H](N(C(=O)Nc2ncc(SCC(=O)O)s2)C2CCCCC2)CC1]

selected from the group consisting of:

a) a crystalline form characterized by an XRPD pattern having peaks at 16.9±0.2, 17.4±0.2, and 20.1±0.2 degrees two theta;

b) a crystalline form characterized by an XRPD pattern having peaks at 11.0±0.2, 11.6±0.2, and 17.8±0.2 degrees two theta;

c) a crystalline form characterized by an XRPD pattern having peaks at 4.3±0.2, 17.4±0.2, and 21.6±0.2 degrees two theta;

d) a crystalline form characterized by an XRPD pattern having peaks at 5.3±0.2, 8.7±0.2, and 26.4±0.2 degrees two theta;

e) a crystalline form characterized by an XRPD pattern having peaks at 5.8±0.2, 17.9±0.2, and 18.9±0.2 degrees two theta;

f) a crystalline form characterized by an XRPD pattern having peaks at 3.8±0.2, 9.5±0.2, and 16.8±0.2 degrees two theta;

g) a crystalline form characterized by an XRPD pattern having peaks at 3.4±0.2, 21.2±0.2, and 21.9±0.2 degrees two theta;

h) a crystalline form characterized by an XRPD pattern having peaks at 3.8±0.2, 5.3±0.2, and 8.5±0.2 degrees two theta;

i) a crystalline form characterized by an XRPD pattern having peaks at 5.0±0.2, 16.8±0.2, and 18.8±0.2 degrees two theta; and j) a crystalline form characterized by an XRPD pattern having peaks at 5.9±0.2, 17.4±0.2, and 18.8±0.2 degrees two theta.

A. Crystalline Form A

In one aspect, the present disclosure relates to a crystalline form of Compound I, characterized by an XRPD pattern having peaks at 16.9±0.2, 17.4±0.2, and 20.1±0.2 degrees two theta. In one aspect, the present disclosure relates to a crystalline form of Compound I, characterized by an XRPD pattern having peaks at 8.7±0.2, 16.9±0.2, 17.4±0.2, and 20.1±0.2 degrees two theta. In one aspect, the crystalline form of Compound I is characterized by an XRPD pattern substantially as shown in FIG. 1.

In one aspect, the crystalline form of Compound I is characterized by the following XRPD pattern in Table 1 expressed in terms of the degree 2θ and relative intensities:

TABLE 1

| Angle (Degree 2θ) | Relative Intensity * (%) |
|---|---|
| 8.7 ± 0.2 | 83 |
| 9.3 ± 0.2 | 18 |
| 11.3 ± 0.2 | 13 |
| 12.1 ± 0.2 | 83 |
| 12.3 ± 0.2 | 49 |
| 13.0 ± 0.2 | 26 |
| 14.4 ± 0.2 | 76 |
| 15.7 ± 0.2 | 11 |
| 16.9 ± 0.2 | 100 |
| 17.4 ± 0.2 | 95 |
| 18.7 ± 0.2 | 48 |
| 18.9 ± 0.2 | 43 |
| 19.2 ± 0.2 | 68 |
| 20.1 ± 0.2 | 99 |
| 20.8 ± 0.2 | 71 |
| 21.4 ± 0.2 | 39 |
| 21.7 ± 0.2 | 63 |
| 22.2 ± 0.2 | 20 |
| 22.7 ± 0.2 | 48 |
| 23.0 ± 0.2 | 36 |
| 23.5 ± 0.2 | 33 |
| 23.7 ± 0.2 | 27 |
| 23.9 ± 0.2 | 31 |
| 24.3 ± 0.2 | 28 |
| 25.9 ± 0.2 | 20 |
| 27.2 ± 0.2 | 30 |
| 27.6 ± 0.2 | 17 |
| 28.3 ± 0.2 | 13 |
| 28.5 ± 0.2 | 12 |

* The relative intensities can change depending on the crystal size and morphology.

Figure 2A:
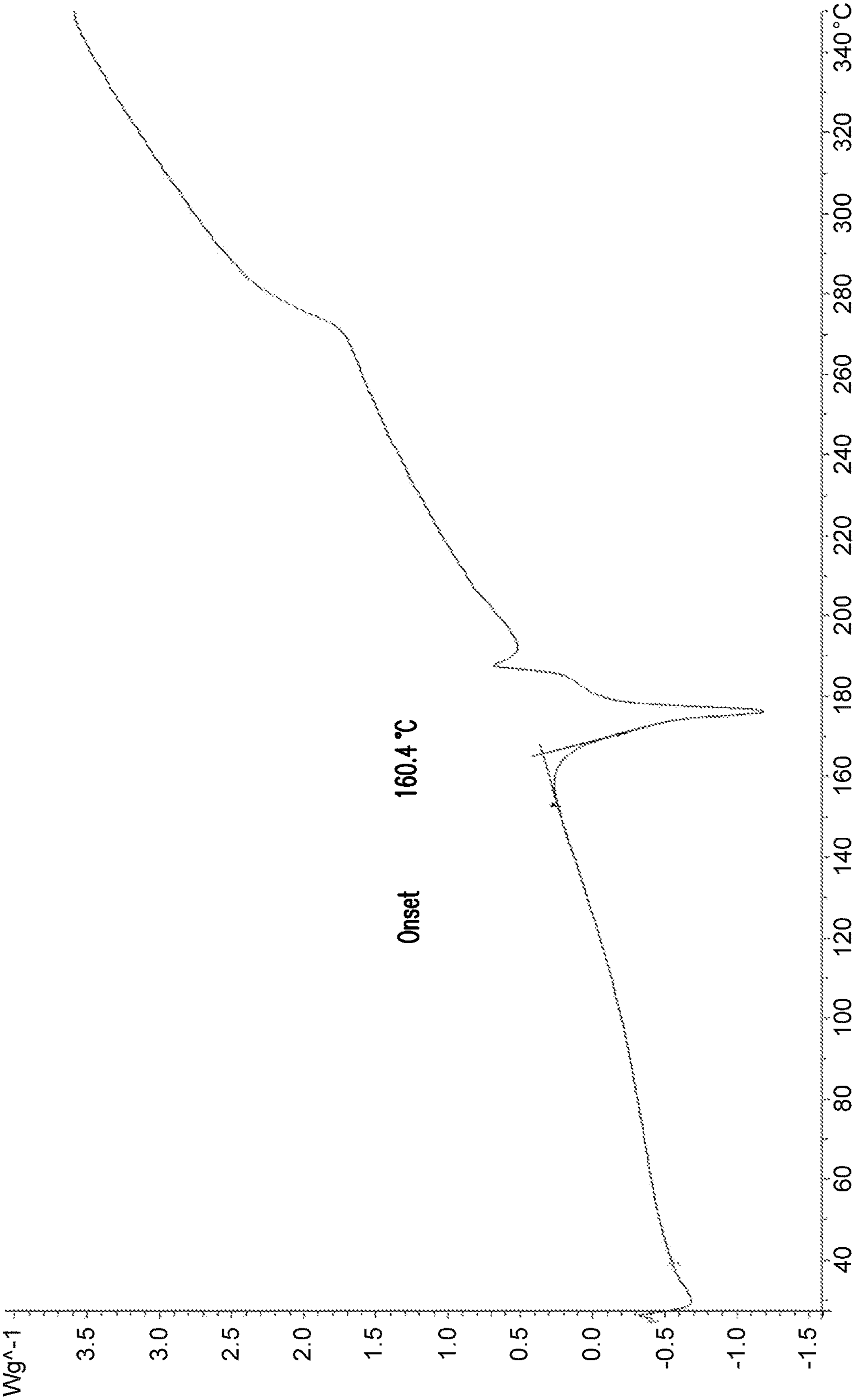
FIG. 2A is a differential scanning calorimetry thermogram ("DSC") corresponding to crystalline Form A.
Figure 2B:
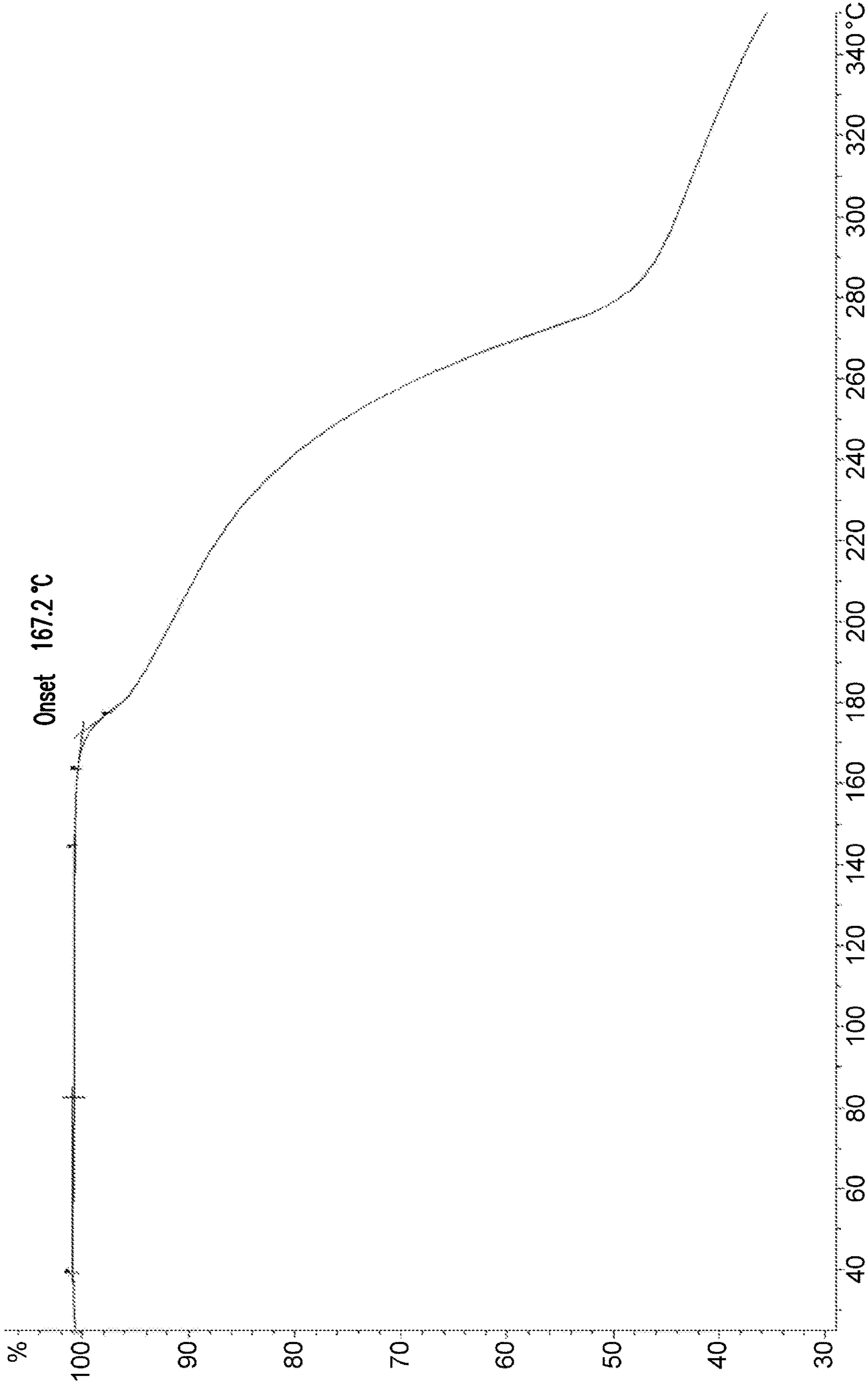
FIG. 2B is a thermogravimetric analysis thermogram ("TGA") corresponding to crystalline Form A.

In one aspect, the crystalline form of Compound I is characterized by an endothermic peak with onset at about 160° C., as determined by DSC. In one aspect, the crystalline form of Compound I is characterized by a DSC profile substantially as shown in FIG. 2A. In one aspect, the crystalline form of Compound I is characterized by a TGA profile substantially as shown in FIG. 2B.

In one aspect, the crystalline form of Compound I is characterized by an IR pattern having peaks at 1099.7±2.0, 1158.0±2.0, and 1313.2±2.0 $cm^{-1}$. In one aspect, the crystalline form of Compound I is characterized by an IR pattern having peaks at 1099.7±2.0, 1158.0±2.0, 1238.7±2.0, and 1313.2±2.0 $cm^{-1}$. In one aspect, the crystalline form of Compound I is characterized by the following IR peaks in Table 2.

TABLE 2

| Position ($cm^{-1}$) | Log(1/R) |
|---|---|
| 713.1 | 0.0120 |
| 723.0 | 0.0108 |
| 747.5 | 0.0083 |
| 777.1 | 0.0053 |
| 790.1 | 0.0063 |
| 807.0 | 0.0094 |
| 857.1 | 0.0116 |
| 893.9 | 0.0125 |
| 913.1 | 0.0114 |
| 941.2 | 0.0054 |
| 950.9 | 0.0054 |
| 1004.4 | 0.0108 |
| 1027.9 | 0.0114 |
| 1048.2 | 0.0122 |
| 1099.7 | 0.0316 |
| 1141.7 | 0.0152 |
| 1158.0 | 0.0284 |
| 1178.0 | 0.0127 |
| 1208.0 | 0.0146 |
| 1238.7 | 0.0256 |
| 1263.6 | 0.0134 |

TABLE 2-continued

| Position ($cm^{-1}$) | Log(1/R) |
|---|---|
| 1313.2 | 0.0440 |
| 1346.4 | 0.0247 |
| 1359.6 | 0.0234 |
| 1398.8 | 0.0132 |
| 1449.9 | 0.0131 |
| 1498.7 | 0.0136 |
| 1544.2 | 0.0282 |
| 1646.7 | 0.0265 |
| 1662.4 | 0.0402 |
| 1698.9 | 0.0109 |
| 1884.3 | 0.0034 |
| 2859.5 | 0.0067 |
| 2931.3 | 0.0109 |
| 3180.1 | 0.0016 |
| 3224.6 | 0.0019 |

Figure 3:
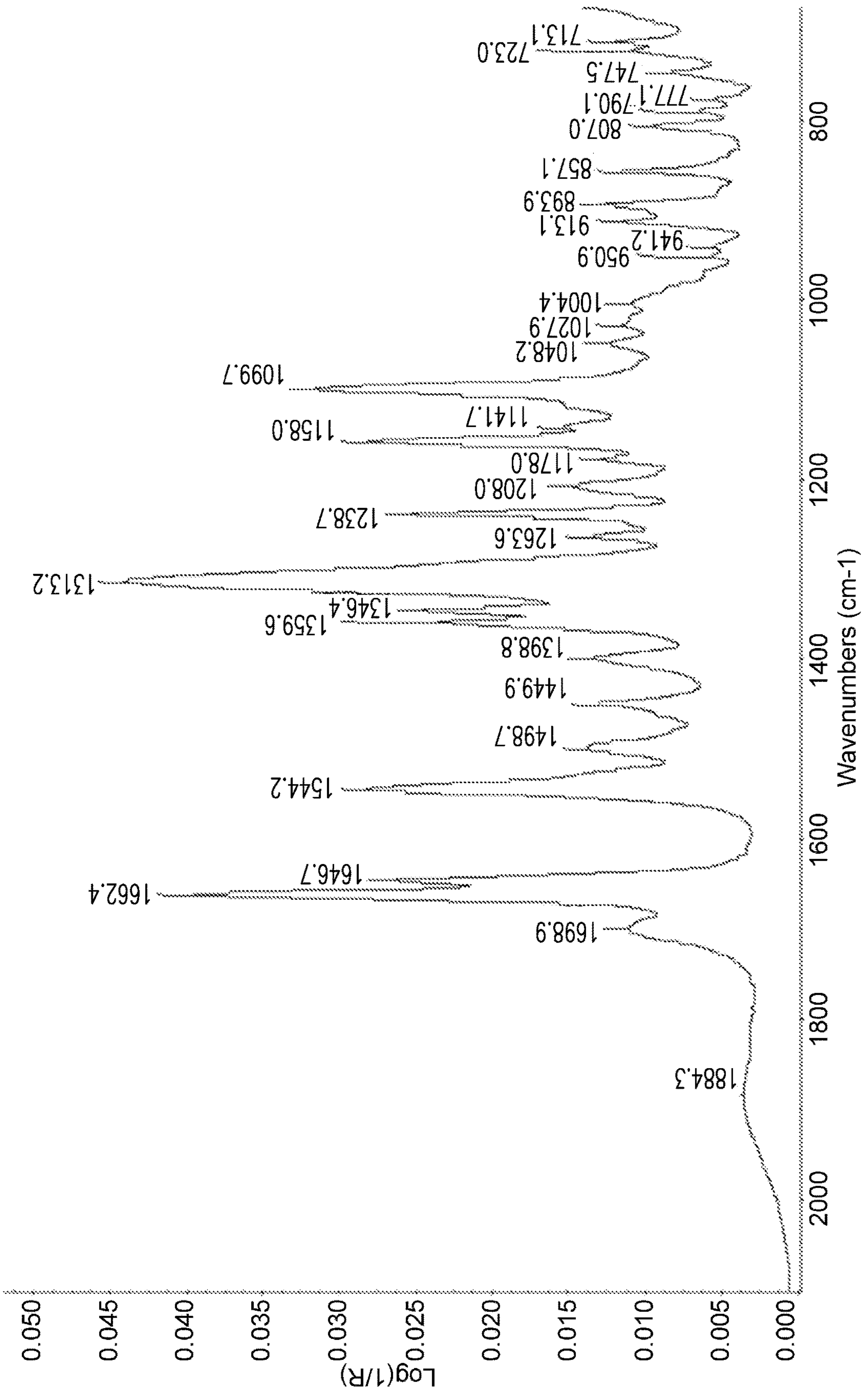
FIG. 3 is an Infrared ("IR") spectrum corresponding to crystalline Form A.

In one aspect, the crystalline form of Compound I is characterized by an IR pattern substantially as shown in FIG. 3.

Figure 4:
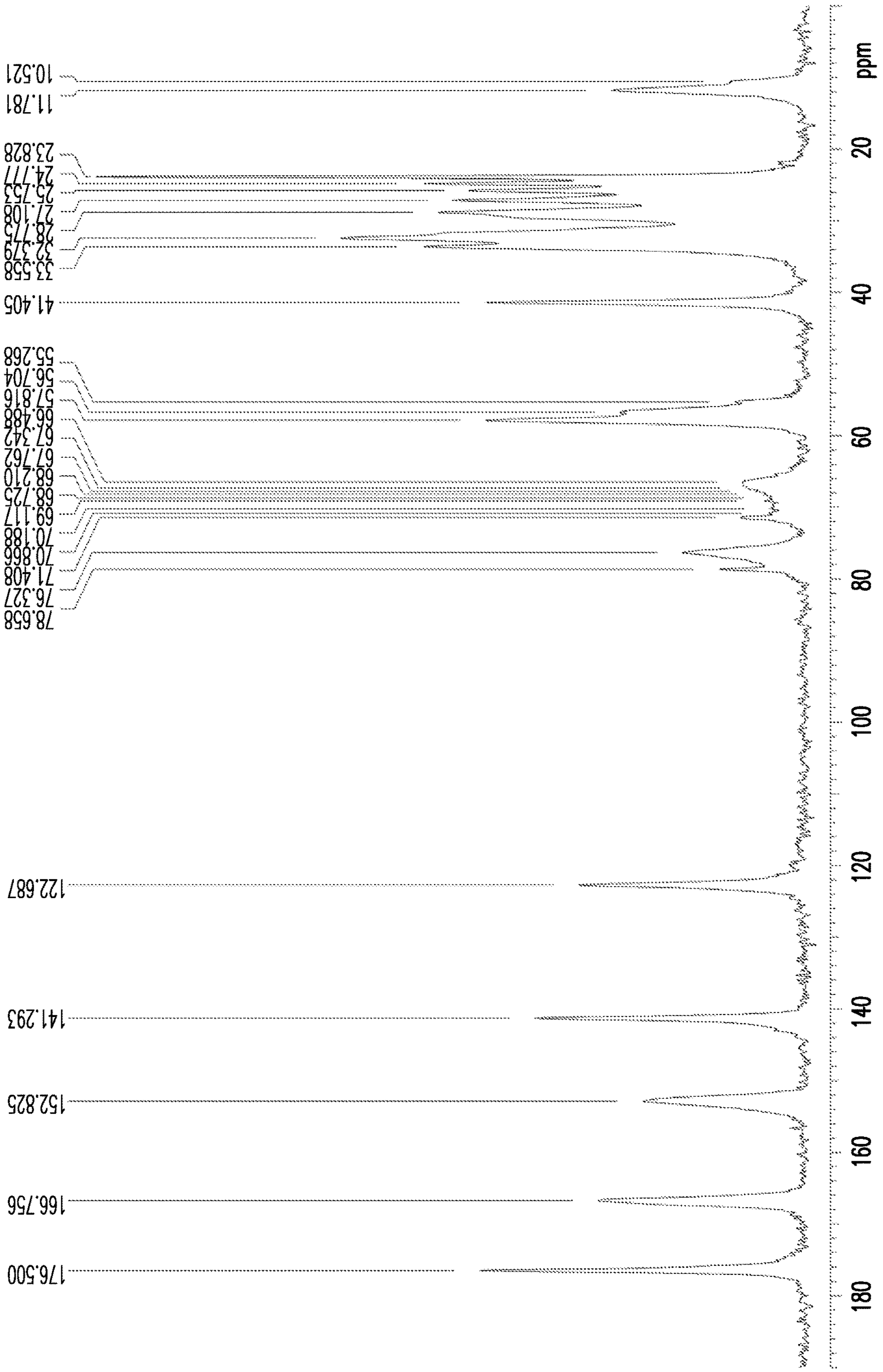
FIG. 4 is a $^{13}C$ solid state NMR corresponding to crystalline Form A.

In one aspect, the crystalline form of Compound I is characterized by a $^{13}C$ solid state NMR substantially as shown in FIG. 4.

In one aspect, the crystalline form is anhydrous as determined by $^{1}H$ NMR.

In one aspect, the crystalline form of Compound I has a unit cell that indexes as primitive monoclinic. In another aspect, the crystalline form of Compound I has a unit cell with an a value of about 10.193 Å, a b value of about 12.256 Å, and a c value of about 18.991 Å. In another aspect, the crystalline form of Compound I has a unit cell with a volume of about 2370.9 $Å^3$.

In one aspect, the crystalline form of Compound I is Form A.

B. Crystalline Form B

In one aspect, the present disclosure relates to a crystalline form of Compound I, characterized by an XRPD pattern having peaks at 11.0±0.2, 11.6±0.2, and 17.8±0.2 degrees two theta. In one aspect, the present disclosure relates to a crystalline form of Compound I, characterized by an XRPD pattern having peaks at 11.0±0.2, 11.6±0.2, 17.8±0.2, and 21.1±0.2 degrees two theta.

Figure 5:
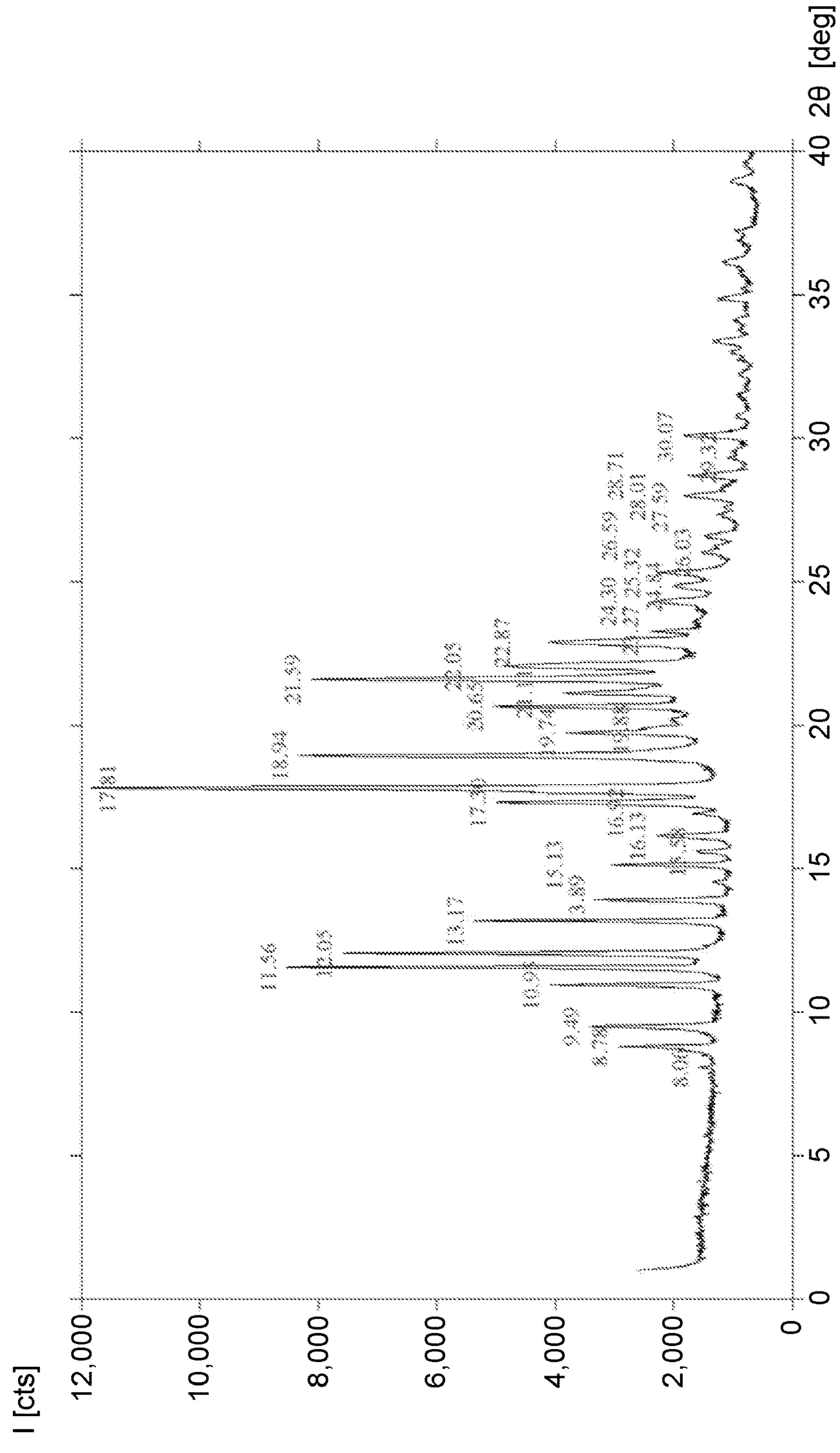
FIG. 5 is an XRPD corresponding to crystalline Form B.

In one aspect, the crystalline form of Compound I is characterized by an XRPD pattern substantially as shown in FIG. 5.

In one aspect, the crystalline form of Compound I is characterized by the following XRPD pattern in Table 3 expressed in terms of the degree 20 and relative intensities:

TABLE 3

| Angle (Degree 2θ) | Relative Intensity * (%) |
|---|---|
| 8.1 ± 0.2 | 13 |
| 8.8 ± 0.2 | 24 |
| 9.5 ± 0.2 | 29 |
| 11 ± 0.2 | 34 |
| 11.6 ± 0.2 | 71 |
| 12.1 ± 0.2 | 64 |
| 13.2 ± 0.2 | 45 |
| 13.9 ± 0.2 | 28 |
| 15.1 ± 0.2 | 26 |
| 15.6 ± 0.2 | 13 |
| 16.1 ± 0.2 | 19 |
| 16.9 ± 0.2 | 14 |
| 17.3 ± 0.2 | 42 |
| 17.8 ± 0.2 | 100 |
| 18.9 ± 0.2 | 70 |
| 19.7 ± 0.2 | 32 |

TABLE 3-continued

| Angle (Degree 2θ) | Relative Intensity * (%) |
|---|---|
| 19.9 ± 0.2 | 21 |
| 20.7 ± 0.2 | 42 |
| 21.1 ± 0.2 | 33 |
| 21.6 ± 0.2 | 68 |
| 22.1 ± 0.2 | 41 |
| 22.9 ± 0.2 | 35 |
| 23.3 ± 0.2 | 20 |
| 24.3 ± 0.2 | 20 |
| 24.8 ± 0.2 | 17 |
| 25.3 ± 0.2 | 19 |
| 26 ± 0.2 | 13 |
| 26.6 ± 0.2 | 13 |
| 27.6 ± 0.2 | 10 |
| 28 ± 0.2 | 15 |
| 28.7 ± 0.2 | 15 |
| 29.3 ± 0.2 | 9 |
| 30.1 ± 0.2 | 15 |

* The relative intensities can change depending on the crystal size and morphology.

Figure 6A:
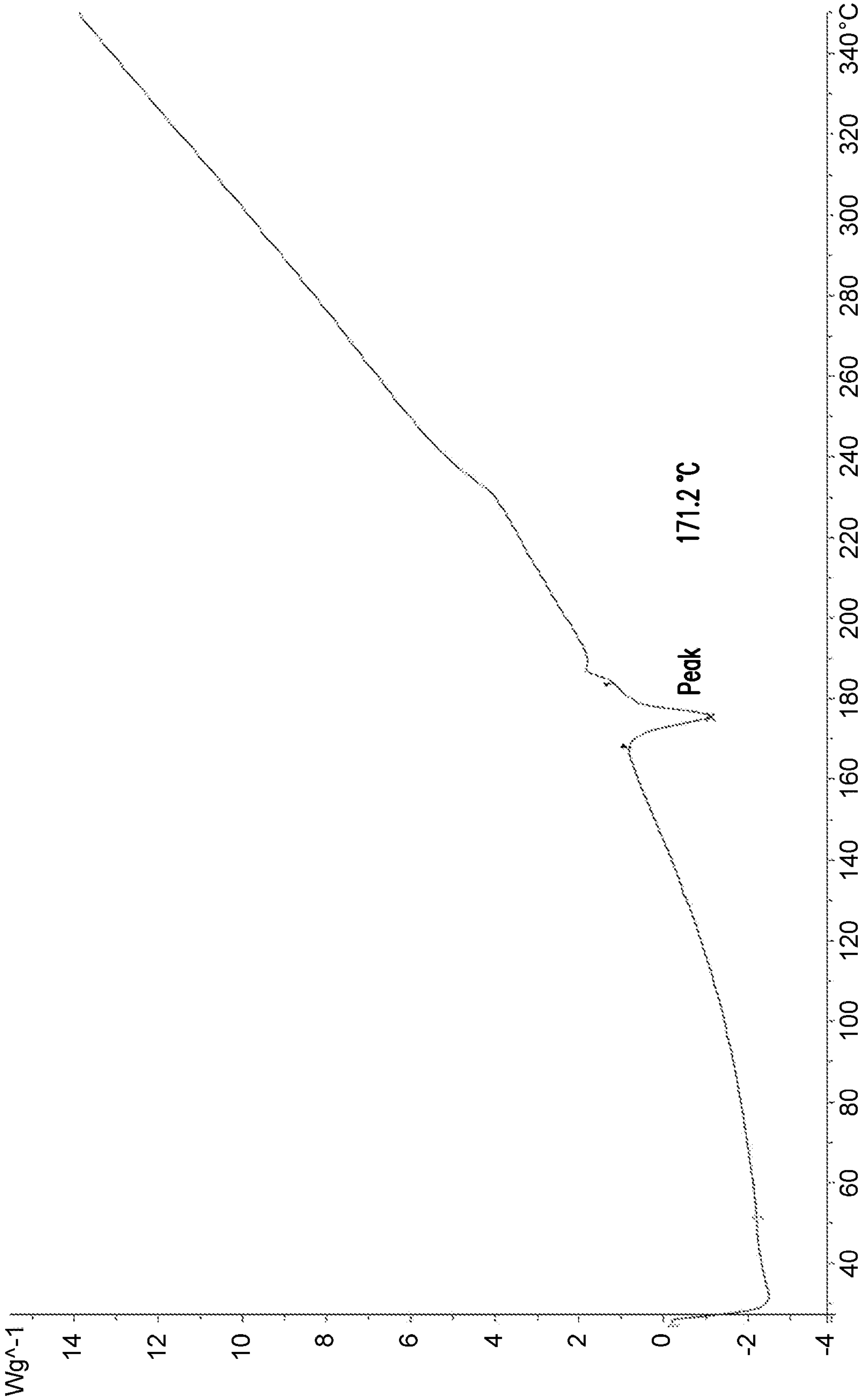
FIG. 6A is a DSC corresponding to crystalline Form B.
Figure 6B:
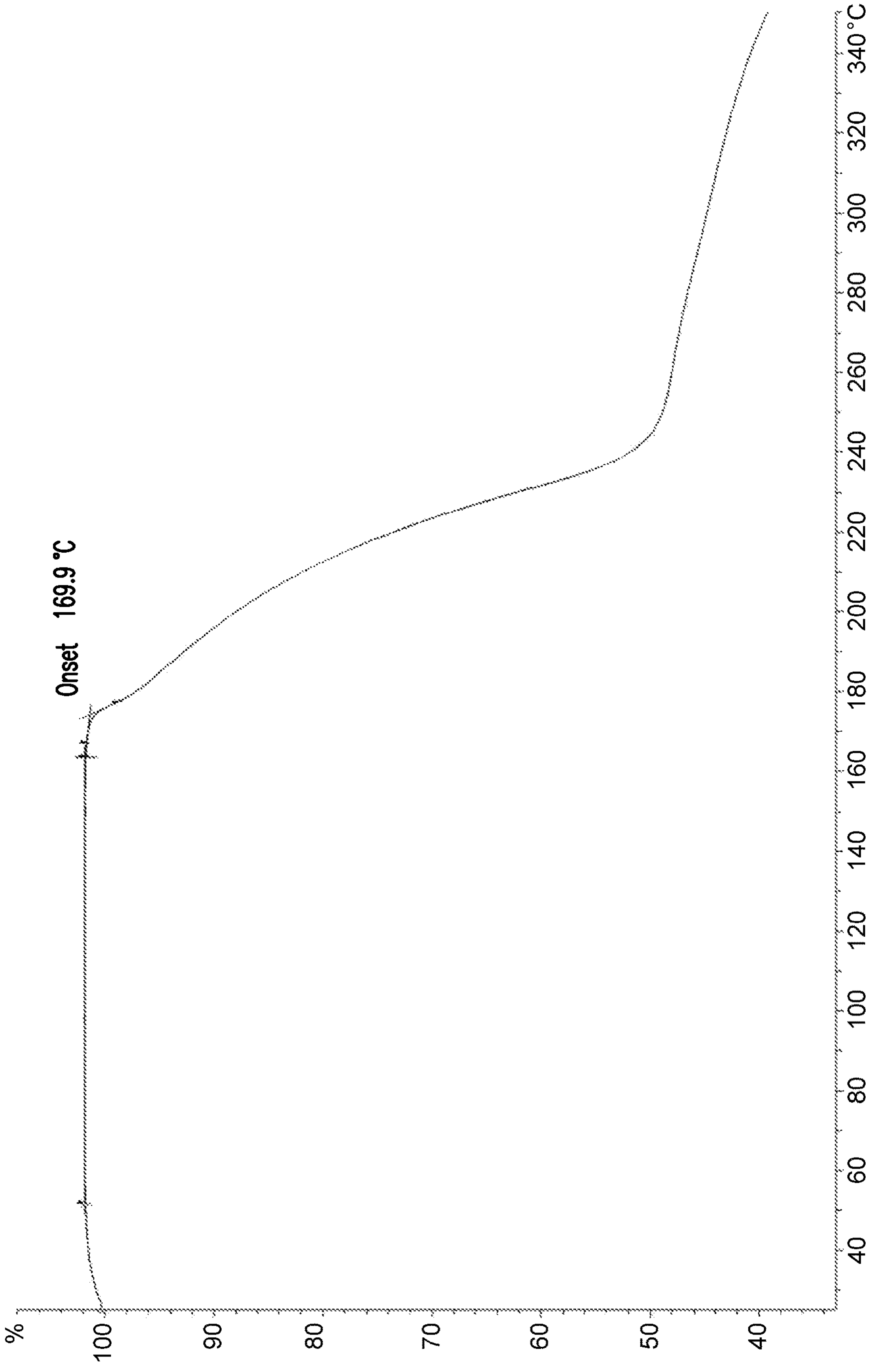
FIG. 6B is a TGA corresponding to crystalline Form B.

In one aspect, the crystalline form of Compound I is characterized by an endothermic peak with onset at about 166° C., as determined by DSC. In one aspect, the crystalline form of Compound I is characterized by a DSC profile substantially as shown in FIG. 6A. In one aspect, the crystalline form of Compound I is characterized by a TGA profile substantially as shown in FIG. 6B.

In one aspect, the crystalline form of Compound I is characterized by an IR pattern having peaks at 1310.1±2.0, 1514.4±2.0, and 1661.3±2.0 $cm^{-1}$. In one aspect, the crystalline form of of Compound I is characterized by an IR pattern having peaks at 1097.3±2.0, 1310.1±2.0, 1541.4±2.0, and 1661.3±2.0 $cm^{-1}$. In one aspect, the crystalline form of Compound I is characterized by the following IR peaks in Table 4.

TABLE 4

| Position ($cm^{-1}$) | Log(1/R) |
|---|---|
| 713.6 | 0.0109 |
| 726.3 | 0.0166 |
| 751.3 | 0.0080 |
| 775.2 | 0.0062 |
| 787.9 | 0.0099 |
| 807.3 | 0.0124 |
| 859.5 | 0.0120 |
| 894.7 | 0.0124 |
| 911.7 | 0.0146 |
| 942.3 | 0.0088 |
| 970.6 | 0.0077 |
| 999.7 | 0.0127 |
| 1018.6 | 0.0127 |
| 1049.1 | 0.0121 |
| 1097.3 | 0.0316 |
| 1122.7 | 0.0162 |
| 1137.9 | 0.0173 |
| 1159.8 | 0.0307 |
| 1183.7 | 0.0146 |
| 1208.6 | 0.0219 |
| 1239.5 | 0.0271 |
| 1265.0 | 0.0193 |
| 1310.1 | 0.0507 |
| 1356.7 | 0.0284 |
| 1399.3 | 0.0165 |
| 1451.7 | 0.0167 |
| 1500.3 | 0.0199 |
| 1541.4 | 0.0346 |
| 1661.3 | 0.0487 |
| 1697.0 | 0.0160 |
| 1886.9 | 0.0075 |
| 2858.8 | 0.0112 |
| 2932.8 | 0.0159 |

TABLE 4-continued

| Position ($cm^{-1}$) | Log(1/R) |
|---|---|
| 3184.1 | 0.0057 |
| 3229.2 | 0.0063 |

Figure 7:
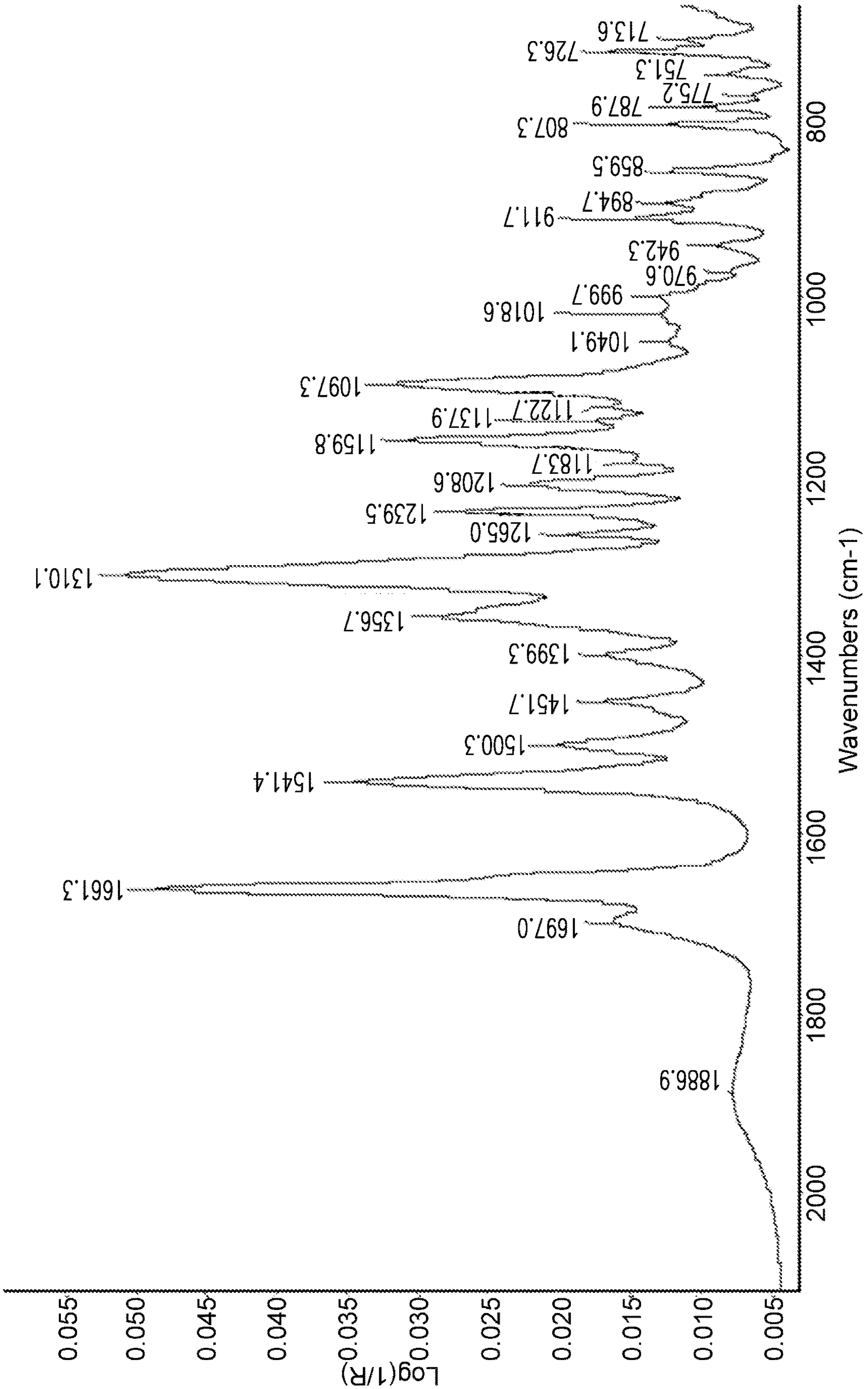
FIG. 7 is an IR spectrum corresponding to crystalline Form B.

In one aspect, the crystalline form of Compound I is characterized by an IR pattern substantially as shown in FIG. 7.

Figure 8:
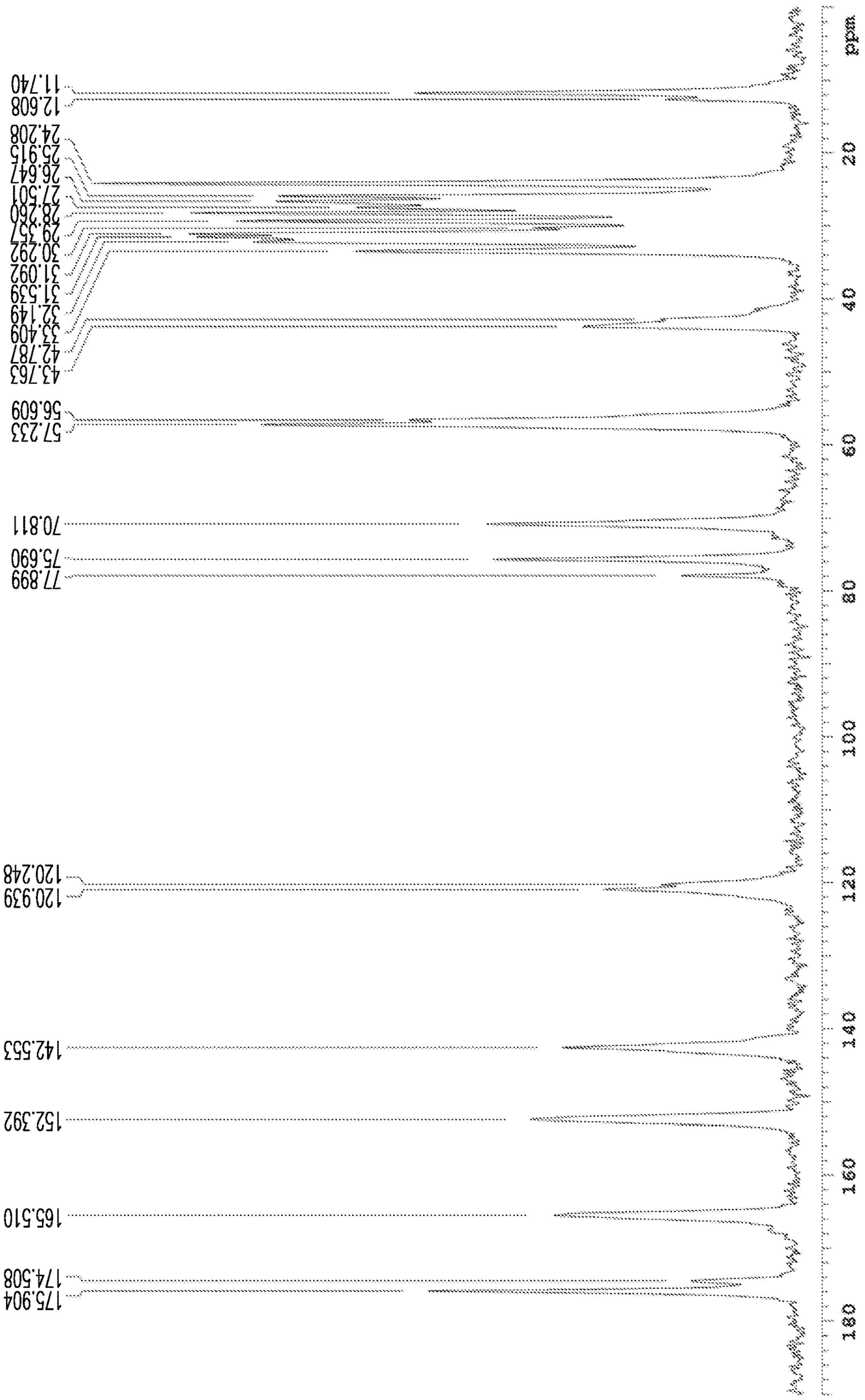
FIG. 8 is a $^{13}C$ solid state NMR corresponding to crystalline Form B.

In one aspect, the crystalline form of of Compound I is characterized by a $^{13}C$ solid state NMR substantially as shown in FIG. 8.

In one aspect, the crystalline form is anhydrous as determined by $^{1}H$ NMR.

In one aspect, the crystalline form of Compound I has a unit cell that indexes as primitive monoclinic. In another aspect, the crystalline form of Compound I has a unit cell with an a value of about 11.028 Å, a b value of about 11.933 Å, and a c value of about 18.737 Å. In another aspect, the crystalline form of Compound I has a unit cell with a volume of about 2449.0 $Å^3$.

In one aspect, the crystalline form of Compound I is Form B.

C. Crystalline Form C

In one aspect, the present disclosure relates to a crystalline form of Compound I, characterized by an XRPD pattern having peaks at 4.3±0.2, 17.4±0.2, and 21.6±0.2 degrees two theta. In one aspect, the present disclosure relates to a crystalline form of Compound I, characterized by an XRPD pattern having peaks at 4.3±0.2, 8.0±0.2, 17.4±0.2, and about 21.6±0.2 degrees two theta.

Figure 9:
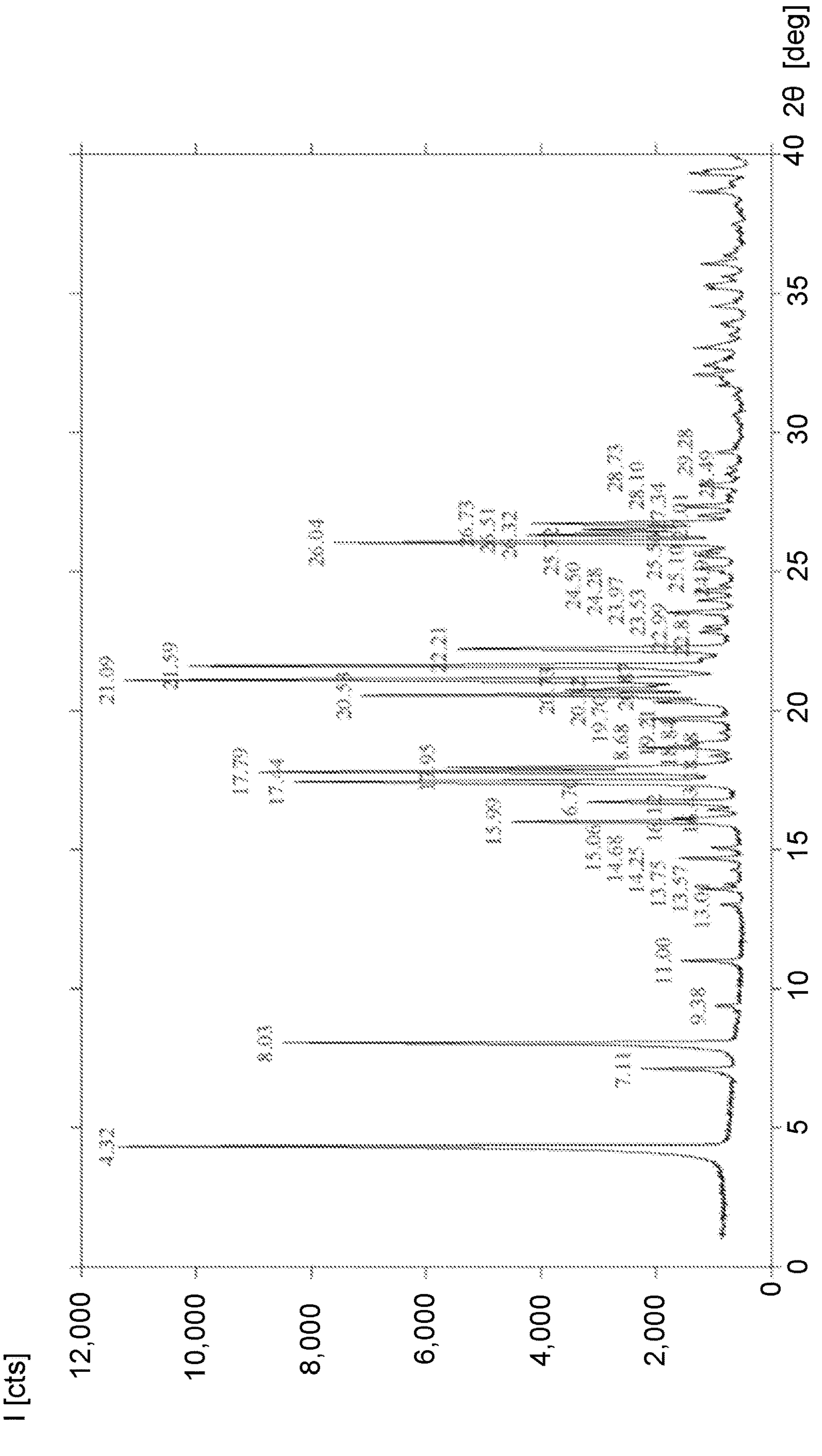
FIG. 9 is an XRPD corresponding to crystalline Form C.

In one aspect, the crystalline form of Compound I is characterized by an XRPD pattern substantially as shown in FIG. 9.

In one aspect, the crystalline form of Compound I is characterized by the following XRPD pattern in Table 5 expressed in terms of the degree 20 and relative intensities:

TABLE 5

| Angle (Degree 2θ) | Relative Intensity * (%) |
|---|---|
| 4.3 ± 0.2 | 100 |
| 7.1 ± 0.2 | 20 |
| 8 ± 0.2 | 71 |
| 9.4 ± 0.2 | 9 |
| 11 ± 0.2 | 14 |
| 13 ± 0.2 | 8 |
| 13.6 ± 0.2 | 11 |
| 13.8 ± 0.2 | 7 |
| 14.3 ± 0.2 | 6 |
| 14.7 ± 0.2 | 14 |
| 15.1 ± 0.2 | 9 |
| 16 ± 0.2 | 39 |
| 16.1 ± 0.2 | 15 |
| 16.4 ± 0.2 | 10 |
| 16.7 ± 0.2 | 28 |
| 17.4 ± 0.2 | 73 |
| 17.8 ± 0.2 | 77 |
| 18 ± 0.2 | 50 |
| 18.4 ± 0.2 | 9 |
| 18.7 ± 0.2 | 20 |
| 18.8 ± 0.2 | 13 |
| 19.2 ± 0.2 | 8 |
| 19.7 ± 0.2 | 20 |
| 20.3 ± 0.2 | 18 |
| 20.5 ± 0.2 | 63 |
| 20.7 ± 0.2 | 32 |
| 20.9 ± 0.2 | 19 |
| 21.1 ± 0.2 | 96 |
| 21.6 ± 0.2 | 88 |

TABLE 5-continued

| Angle (Degree 2θ) | Relative Intensity * (%) |
|---|---|
| 22.2 ± 0.2 | 48 |
| 22.8 ± 0.2 | 11 |
| 23 ± 0.2 | 10 |
| 23.5 ± 0.2 | 15 |
| 24 ± 0.2 | 11 |
| 24.3 ± 0.2 | 12 |
| 24.5 ± 0.2 | 8 |
| 25 ± 0.2 | 8 |
| 25.1 ± 0.2 | 12 |
| 25.6 ± 0.2 | 11 |
| 25.7 ± 0.2 | 10 |
| 26 ± 0.2 | 67 |
| 26.3 ± 0.2 | 37 |
| 26.5 ± 0.2 | 29 |
| 26.7 ± 0.2 | 36 |
| 27 ± 0.2 | 11 |
| 27.3 ± 0.2 | 13 |
| 28.1 ± 0.2 | 10 |
| 28.5 ± 0.2 | 7 |
| 28.7 ± 0.2 | 7 |
| 29.3 ± 0.2 | 8 |

* The relative intensities can change depending on the crystal size and morphology.

Figure 10A:
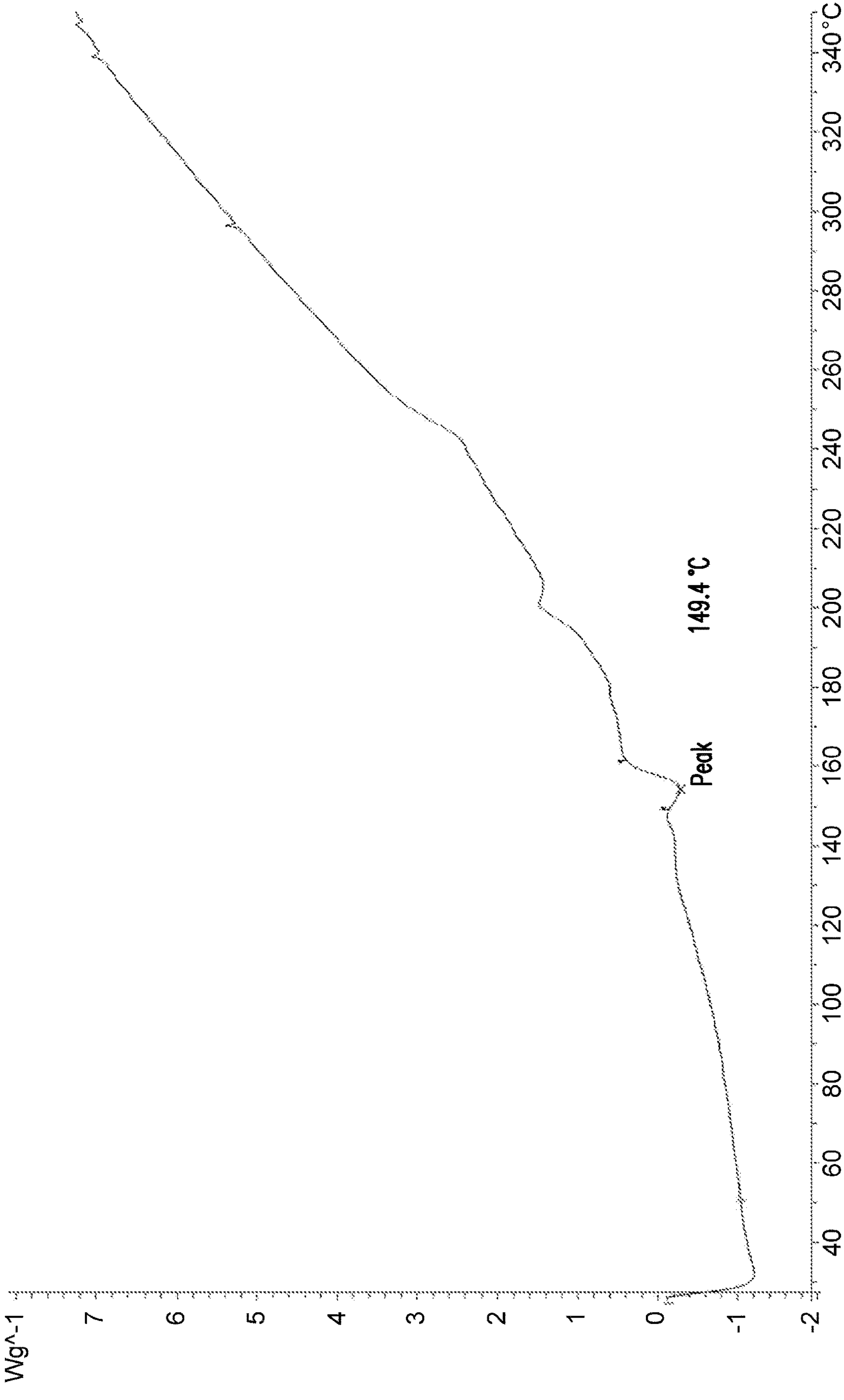
FIG. 10A is a DSC corresponding to crystalline Form C.
Figure 10B:
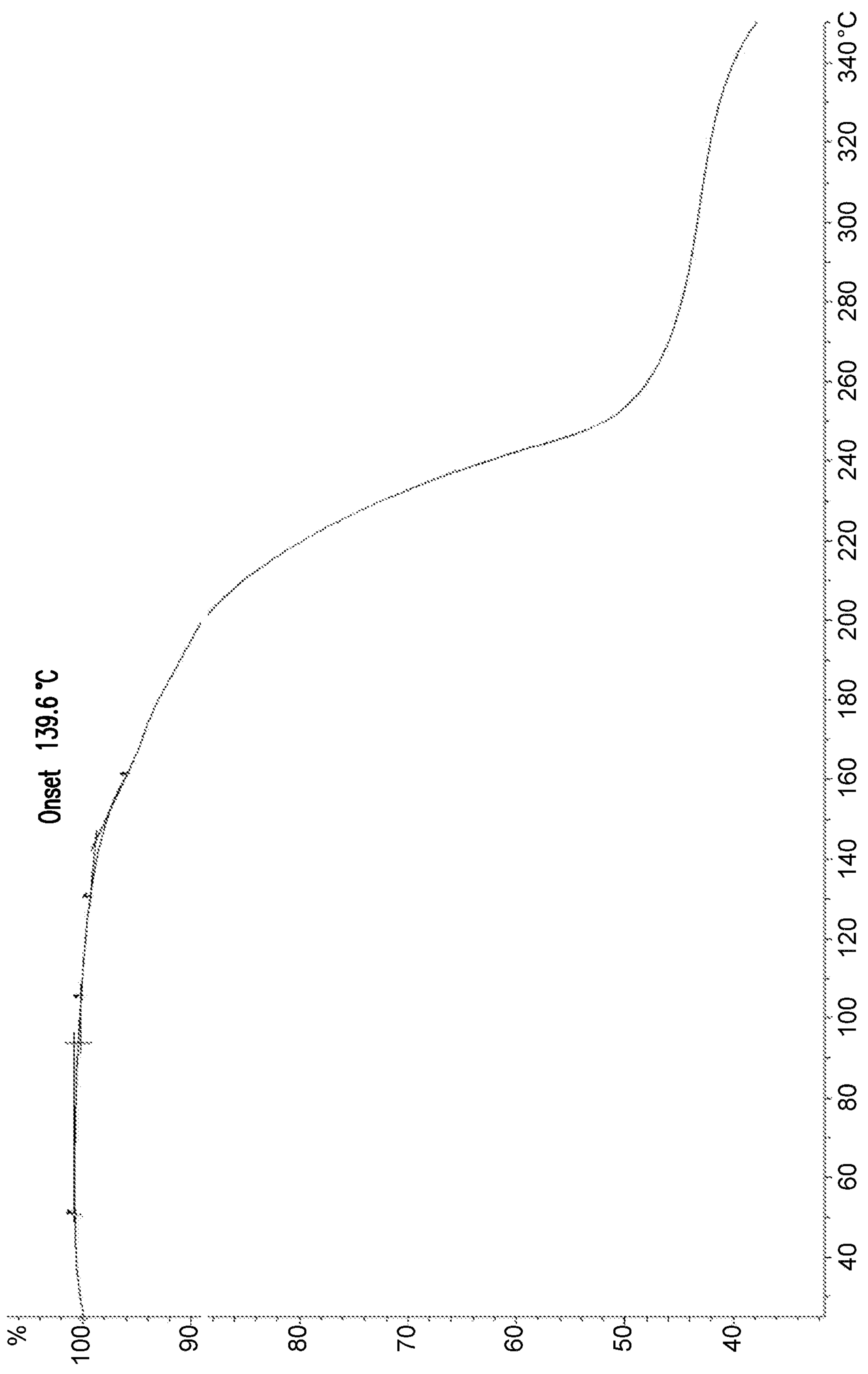
FIG. 10B is a TGA corresponding to crystalline Form C.

In one aspect, the crystalline form of Compound I is characterized by an endothermic peak with onset at about 149° C., as determined by DSC. In one aspect, the crystalline form of Compound I is characterized by a DSC profile substantially as shown in FIG. 10A. In one aspect, the crystalline form of Compound I is characterized by a TGA profile substantially as shown in FIG. 10B.

In one aspect, the crystalline form is a solvate as determined by $^{1}H$ NMR. In one aspect, the crystalline form of Compound I is a dichloromethane solvate.

In one aspect, the crystalline form of Compound I has a unit cell that indexes as primitive monoclinic. In another aspect, the crystalline form of Compound I has a unit cell with an a value of about 5.541 Å, a b value of about 13.040 Å, and a c value of about 40.818 Å. In another aspect, the crystalline form of Compound I has a unit cell with a volume of about 2947.6 $Å^3$.

In one aspect, the crystalline form of Compound I is Form C.

D. Crystalline Form D

In one aspect, the present disclosure relates to a crystalline form of Compound I, characterized by an XRPD pattern having peaks at 5.3±0.2, 8.7±0.2, and 26.4±0.2 degrees two theta. In one aspect, the present disclosure relates to a crystalline form of Compound I, characterized by an XRPD pattern having peaks at 5.3±0.2, 8.7±0.2, 18.2±0.2, and 26.4±0.2 degrees two theta.

Figure 11:
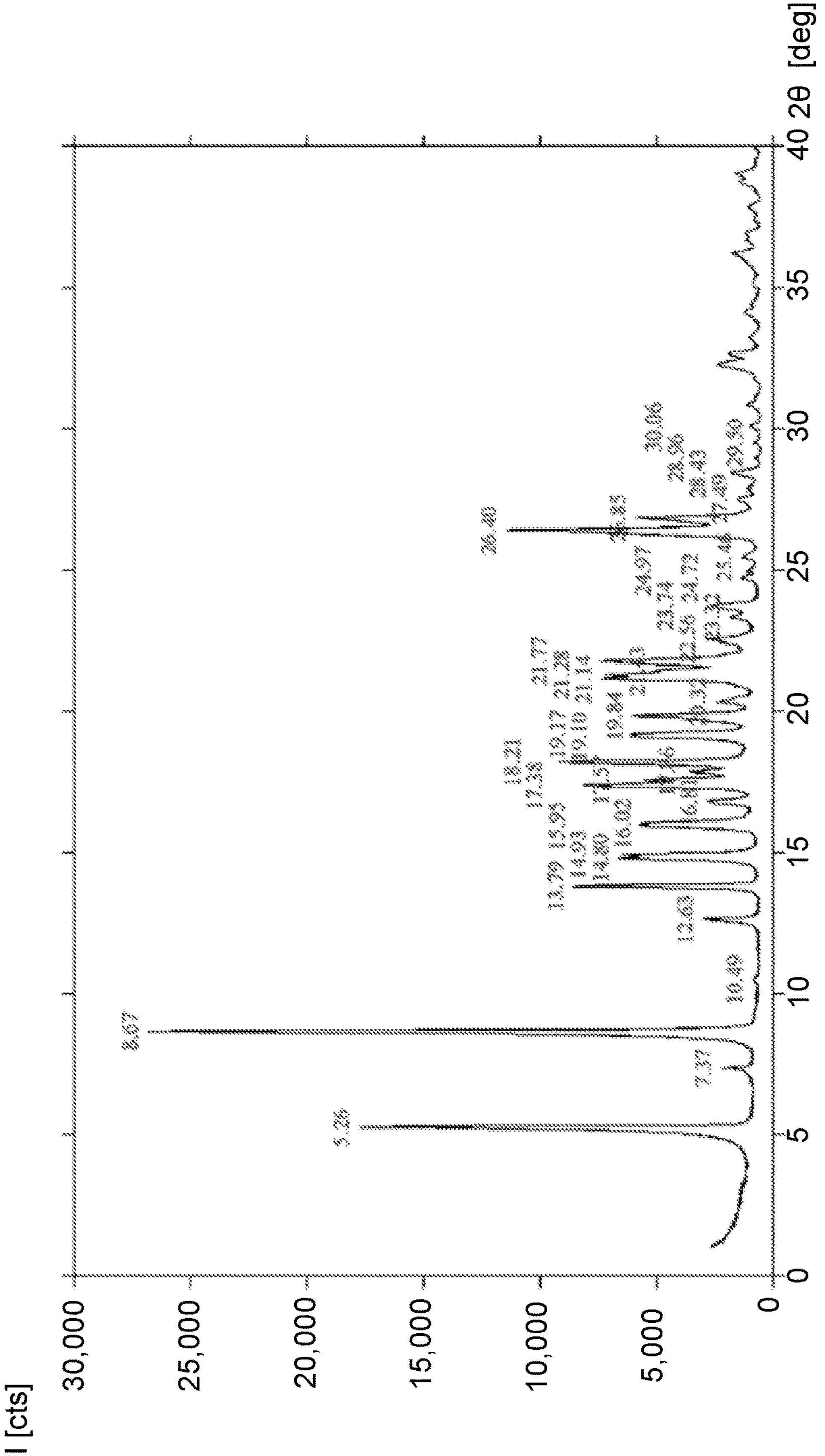
FIG. 11 is an XRPD corresponding to crystalline Form D.

In one aspect, the crystalline form of Compound I is characterized by an XRPD pattern substantially as shown in FIG. 11.

In one aspect, the crystalline form of Compound I is characterized by the following XRPD pattern in Table 6 expressed in terms of the degree 20 and relative intensities:

TABLE 6

| Angle (Degree 2θ) | Relative Intensity * (%) |
|---|---|
| 5.3 ± 0.2 | 66 |
| 7.4 ± 0.2 | 8 |
| 8.7 ± 0.2 | 100 |
| 10.5 ± 0.2 | 3 |
| 12.6 ± 0.2 | 11 |

TABLE 6-continued

| Angle (Degree 2θ) | Relative Intensity * (%) |
|---|---|
| 13.8 ± 0.2 | 32 |
| 14.8 ± 0.2 | 25 |
| 14.9 ± 0.2 | 24 |
| 16.0 ± 0.2 | 22 |
| 16.0 ± 0.2 | 21 |
| 16.8 ± 0.2 | 11 |
| 17.4 ± 0.2 | 31 |
| 17.6 ± 0.2 | 21 |
| 17.9 ± 0.2 | 13 |
| 18.2 ± 0.2 | 34 |
| 19.1 ± 0.2 | 23 |
| 19.2 ± 0.2 | 23 |
| 19.8 ± 0.2 | 23 |
| 20.3 ± 0.2 | 9 |
| 21.1 ± 0.2 | 28 |
| 21.3 ± 0.2 | 27 |
| 21.4 ± 0.2 | 19 |
| 21.8 ± 0.2 | 28 |
| 22.6 ± 0.2 | 11 |
| 23.3 ± 0.2 | 7 |
| 23.7 ± 0.2 | 10 |
| 24.7 ± 0.2 | 5 |
| 25.0 ± 0.2 | 4 |
| 25.5 ± 0.2 | 5 |
| 26.4 ± 0.2 | 43 |
| 26.9 ± 0.2 | 22 |
| 27.5 ± 0.2 | 6 |
| 28.4 ± 0.2 | 7 |
| 29.0 ± 0.2 | 3 |
| 29.5 ± 0.2 | 3 |
| 30.1 ± 0.2 | 4 |

* The relative intensities can change depending on the crystal size and morphology.

Figure 12A:
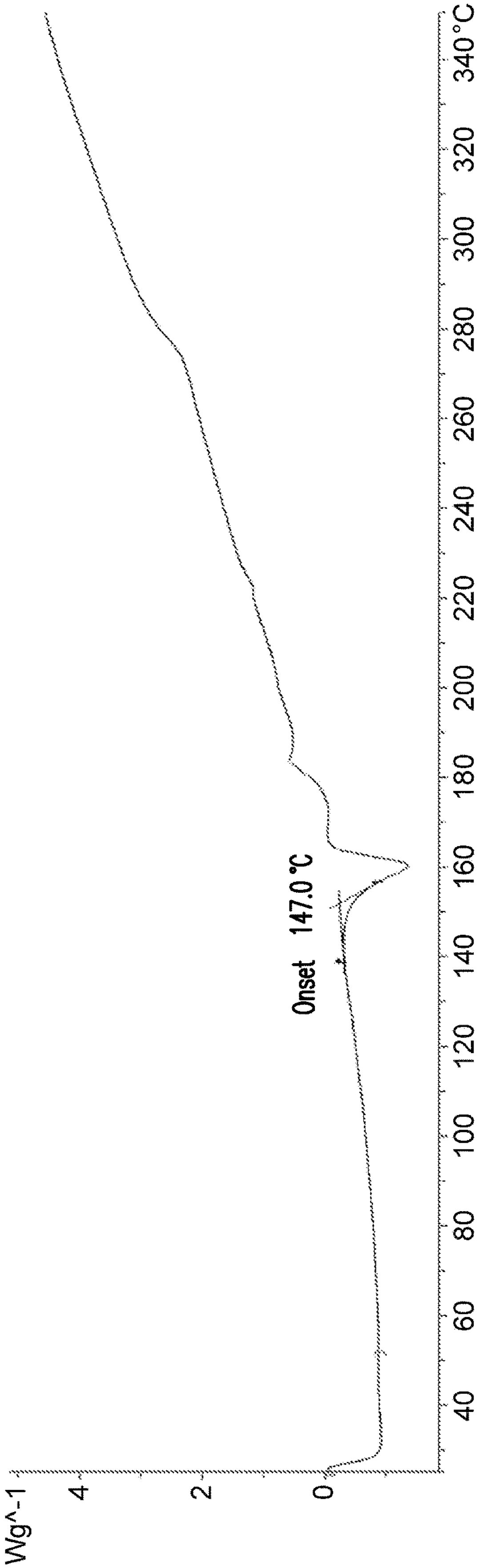
FIG. 12A is a DSC corresponding to crystalline Form D.
Figure 12B:
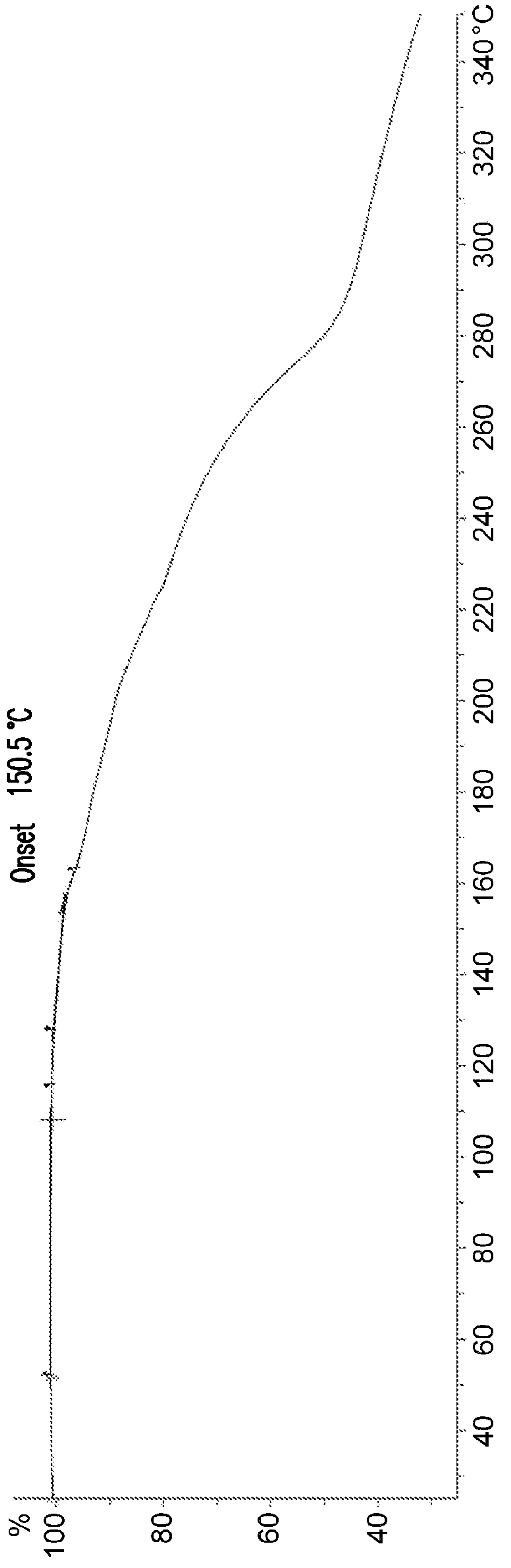
FIG. 12B is a TGA corresponding to crystalline Form D.

In one aspect, the crystalline form of Compound I is characterized by an endothermic peak with onset at about 147° C., as determined by DSC. In one aspect, the crystalline form of Compound I is characterized by a DSC profile substantially as shown in FIG. 12A. In one aspect, the crystalline form of Compound I is characterized by a TGA profile substantially as shown in FIG. 12B.

Figure 13:
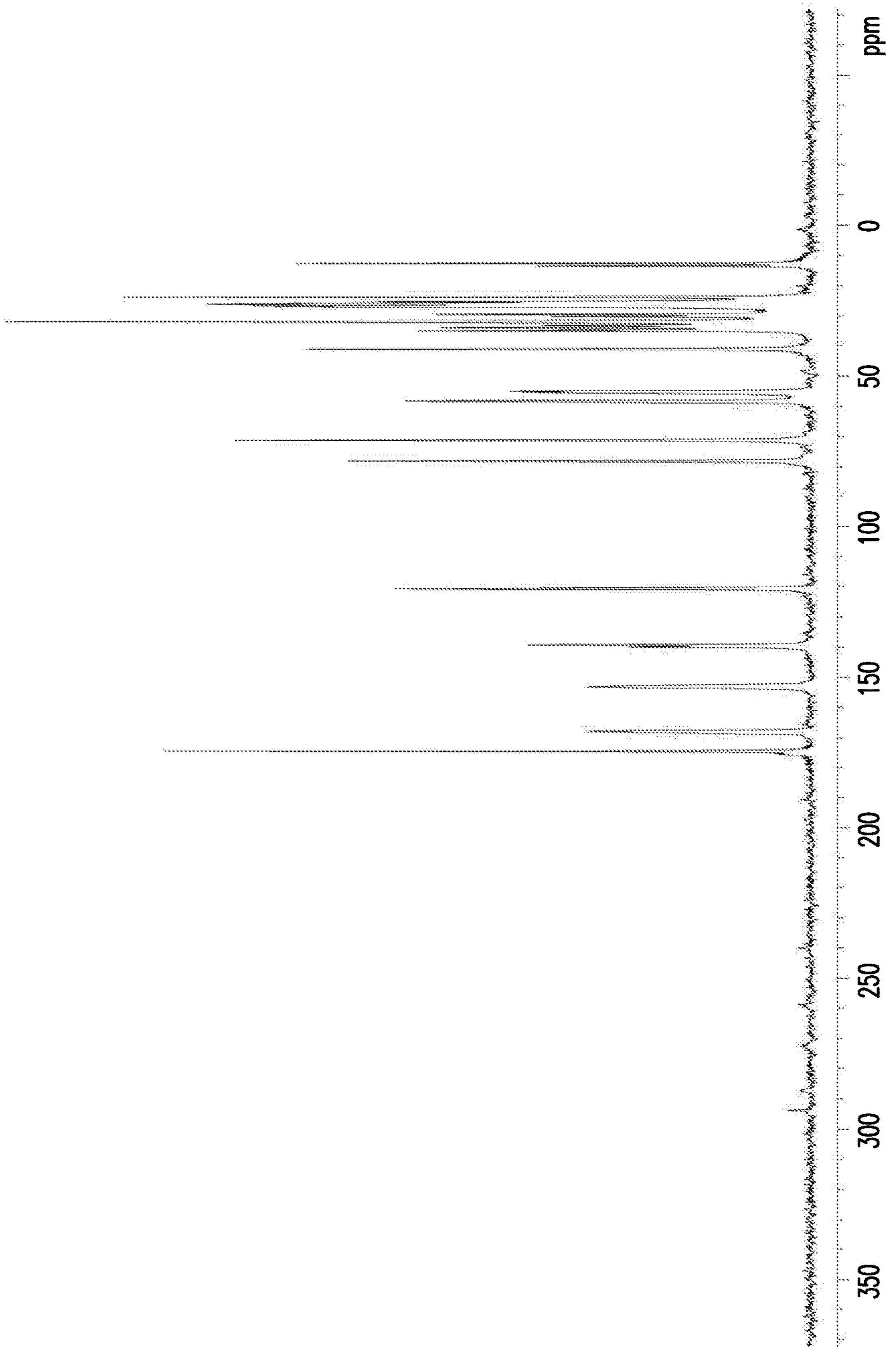
FIG. 13 is a $^{13}C$ solid state NMR corresponding to crystalline Form D.

In one aspect, the crystalline form of Compound I is characterized by a $^{13}C$ solid state NMR substantially similar to FIG. 13.

In one aspect, the crystalline form of Compound I is Form D.

E. Crystalline Form E

In one aspect, the present disclosure relates to a crystalline form of Compound I, characterized by an XRPD pattern having peaks at 5.8±0.2, 17.9±0.2, and 18.9±0.2 degrees two theta. In one aspect, the present disclosure relates to a crystalline form of Compound I, characterized by an XRPD pattern having peaks at 5.8±0.2, 17.9±0.2, 18.9±0.2, and 20.7±0.2 degrees two theta.

Figure 14:
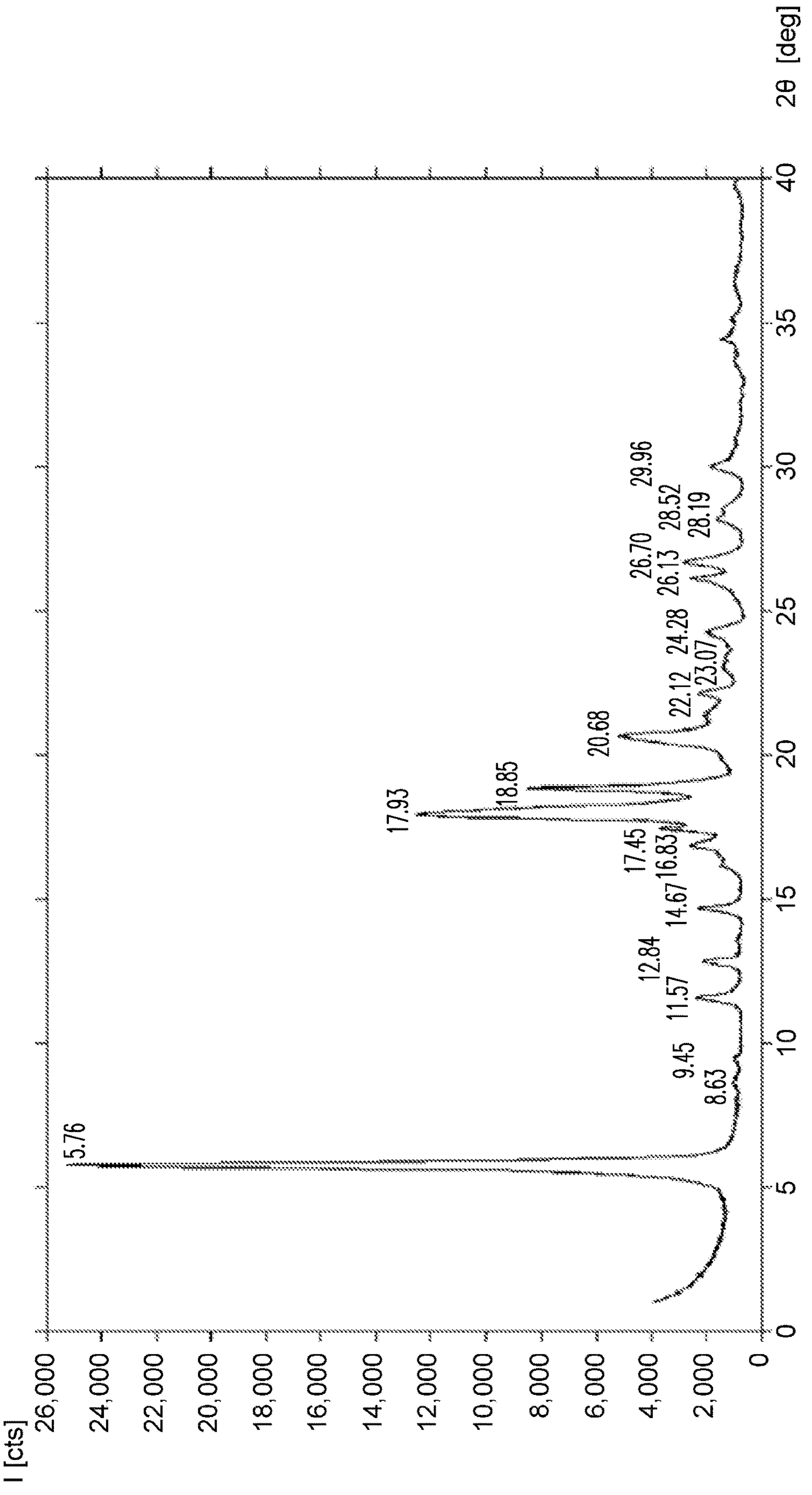
FIG. 14 is an XRPD corresponding to crystalline Form E.

In one aspect, the crystalline form of Compound I is characterized by an XRPD pattern substantially as shown in FIG. 14.

In one aspect, the crystalline form of Compound I is characterized by the following XRPD pattern in Table 7 expressed in terms of the degree 20 and relative intensities:

TABLE 7

| Angle (Degree 2θ) | Relative Intensity * (%) |
|---|---|
| 5.8 ± 0.2 | 100 |
| 8.6 ± 0.2 | 4 |
| 9.5 ± 0.2 | 4 |
| 11.6 ± 0.2 | 9 |
| 12.8 ± 0.2 | 8 |
| 14.7 ± 0.2 | 9 |
| 16.9 ± 0.2 | 10 |
| 17.5 ± 0.2 | 14 |
| 17.9 ± 0.2 | 49 |
| 18.9 ± 0.2 | 34 |
| 20.7 ± 0.2 | 20 |
| 22.1 ± 0.2 | 9 |
| 23.1 ± 0.2 | 5 |
| 24.3 ± 0.2 | 8 |
| 26.1 ± 0.2 | 10 |
| 26.7 ± 0.2 | 11 |
| 28.2 ± 0.2 | 6 |
| 28.5 ± 0.2 | 6 |
| 30.0 ± 0.2 | 7 |

* The relative intensities can change depending on the crystal size and morphology.

Figure 15A:
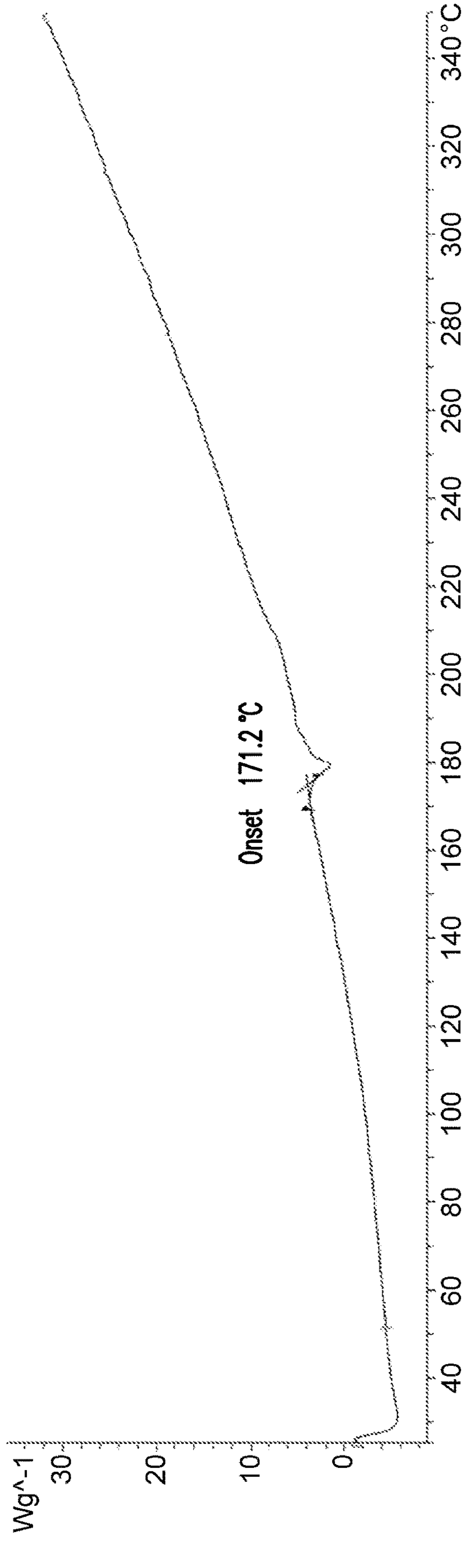
FIG. 15A is a DSC corresponding to crystalline Form E.
Figure 15B:
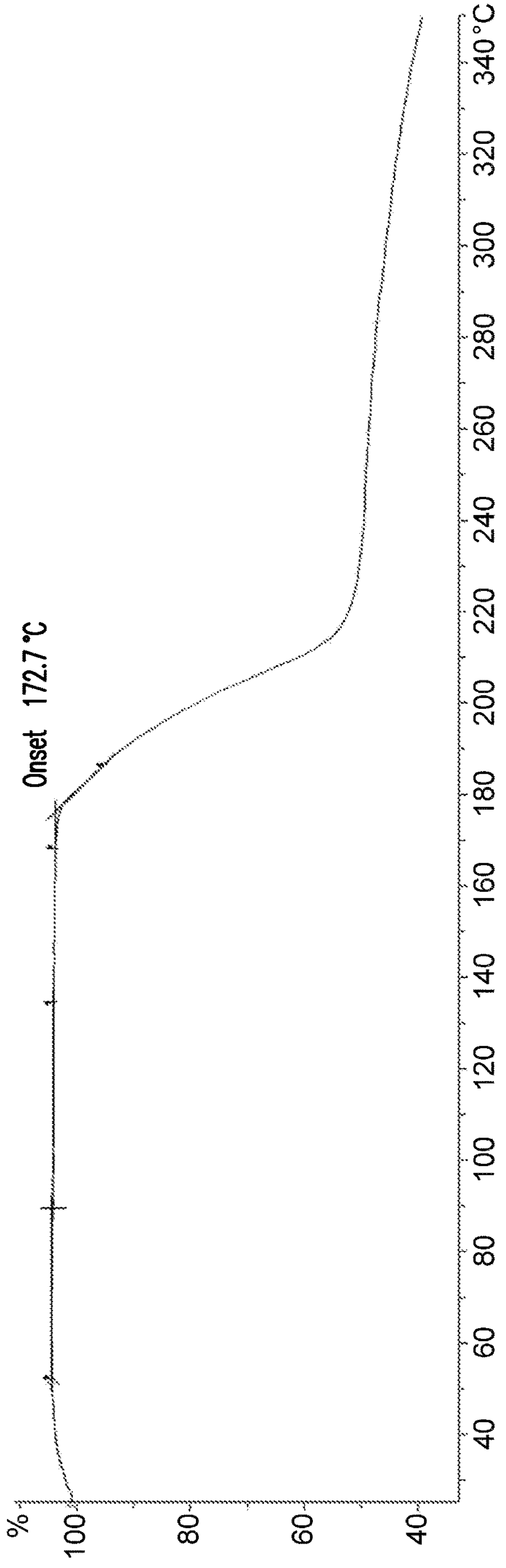
FIG. 15B is a TGA corresponding to crystalline Form E.

In one aspect, the crystalline form of Compound I is characterized by an endothermic peak with onset at about 171° C., as determined by DSC. In one aspect, the crystalline form of Compound I is characterized by a DSC profile substantially as shown in FIG. 15A. In one aspect, the crystalline form of Compound I is characterized by a TGA profile substantially as shown in FIG. 15B.

In one aspect, the crystalline form of Compound I is Form E.

F. Crystalline Form F

In one aspect, the present disclosure relates to a crystalline form of Compound I, characterized by an XRPD pattern having peaks at 3.8±0.2, 9.5±0.2, and 16.8±0.2 degrees two theta. In one aspect, the present disclosure relates to a crystalline form of Compound I, characterized by an XRPD pattern having peaks at 3.8±0.2, 9.5±0.2, 16.8±0.2, and 17.9±0.2 degrees two theta.

Figure 16:
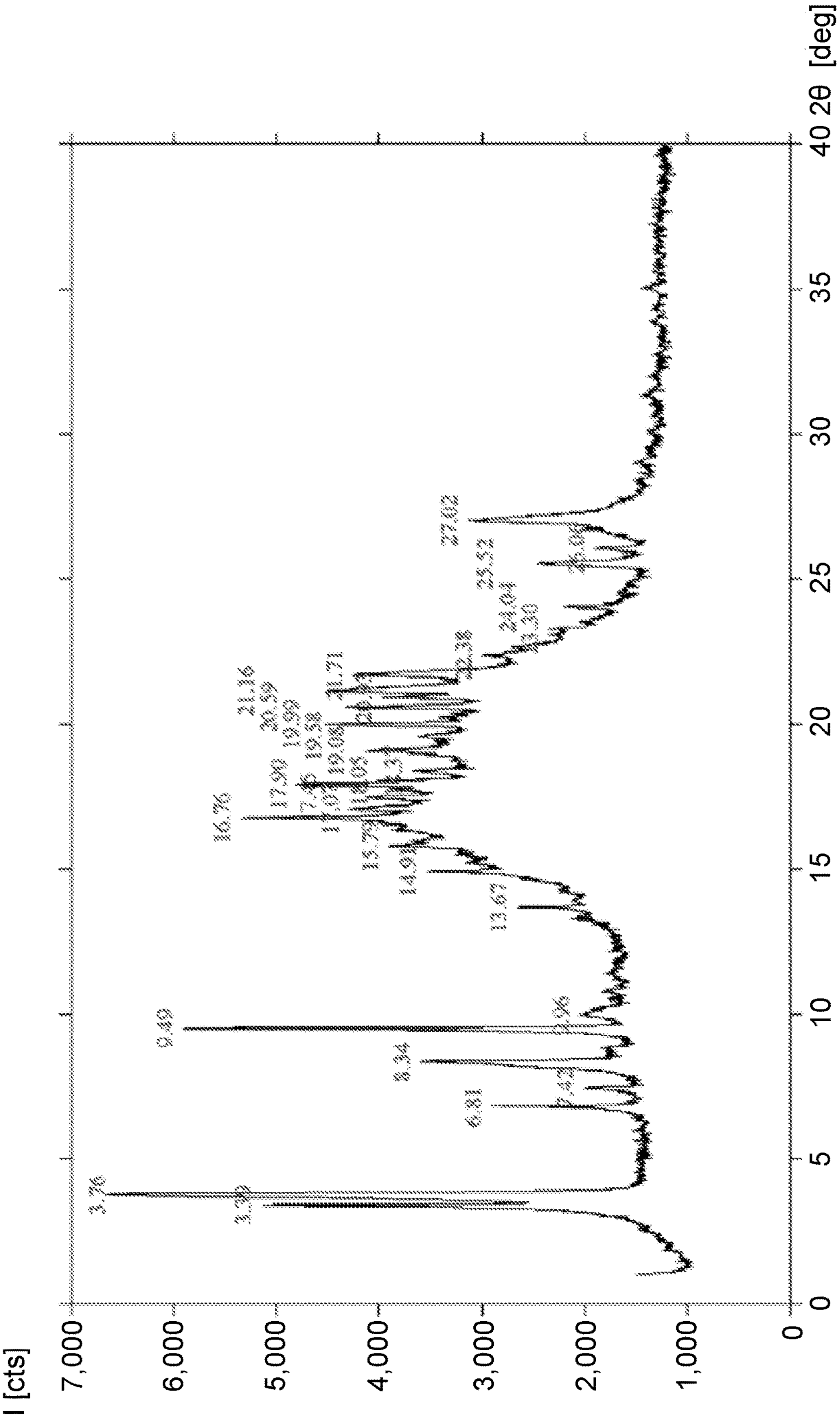
FIG. 16 is an XRPD corresponding to crystalline Form F.

In one aspect, the crystalline form of Compound I is characterized by an XRPD pattern substantially as shown in FIG. 16.

In one aspect, the crystalline form of Compound I is characterized by the following XRPD pattern in Table 8 expressed in terms of the degree 20 and relative intensities:

TABLE 8

| Angle (Degree 2θ) | Relative Intensity * (%) |
|---|---|
| 3.4 ± 0.2 | 76 |
| 3.8 ± 0.2 | 100 |
| 6.8 ± 0.2 | 43 |
| 7.4 ± 0.2 | 30 |
| 8.3 ± 0.2 | 53 |
| 9.5 ± 0.2 | 89 |
| 10.0 ± 0.2 | 31 |
| 13.7 ± 0.2 | 40 |
| 14.9 ± 0.2 | 53 |
| 15.8 ± 0.2 | 59 |
| 16.8 ± 0.2 | 80 |
| 17.1 ± 0.2 | 63 |
| 17.5 ± 0.2 | 62 |
| 17.9 ± 0.2 | 72 |
| 18.1 ± 0.2 | 60 |
| 18.4 ± 0.2 | 54 |
| 19.1 ± 0.2 | 60 |
| 19.6 ± 0.2 | 54 |
| 20.0 ± 0.2 | 67 |
| 20.6 ± 0.2 | 65 |
| 20.9 ± 0.2 | 58 |
| 21.2 ± 0.2 | 67 |
| 21.7 ± 0.2 | 64 |
| 22.4 ± 0.2 | 45 |

TABLE 8-continued

| Angle (Degree 2θ) | Relative Intensity * (%) |
|---|---|
| 23.3 ± 0.2 | 34 |
| 24.0 ± 0.2 | 32 |
| 25.5 ± 0.2 | 37 |
| 26.1 ± 0.2 | 29 |
| 27.0 ± 0.2 | 47 |

* The relative intensities can change depending on the crystal size and morphology.

In one aspect, the crystalline form of Compound I is Form F.

G. Crystalline Form G

In one aspect, the present disclosure relates to a crystalline form of Compound I, characterized by an XRPD pattern having peaks at 3.4±0.2, 21.2±0.2, and 21.9±0.2 degrees two theta. In one aspect, the present disclosure relates to a crystalline form of Compound I, characterized by an XRPD pattern having peaks at 3.4±0.2, 21.2±0.2, 21.9±0.2, and 22.4±0.2 degrees two theta.

Figure 17:
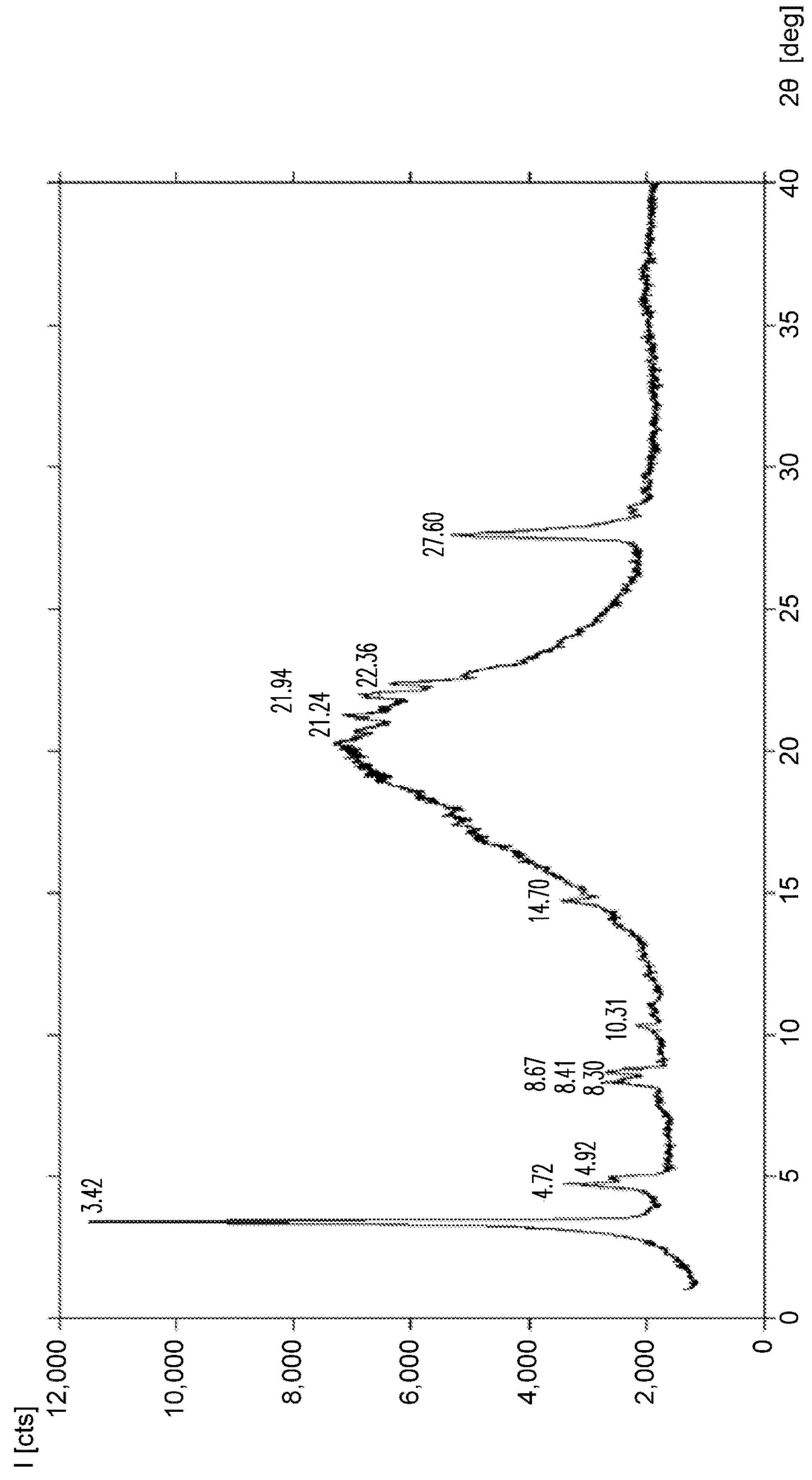
FIG. 17 is an XRPD corresponding to crystalline Form G.

In one aspect, the crystalline form of Compound I is characterized by an XRPD pattern substantially as shown in FIG. 17.

In one aspect, the crystalline form of Compound I is characterized by the following XRPD pattern in Table 9 expressed in terms of the degree 20 and relative intensities:

TABLE 9

| Angle (Degree 2θ) | Relative Intensity * (%) |
|---|---|
| 3.4 ± 0.2 | 100 |
| 4.7 ± 0.2 | 30 |
| 4.9 ± 0.2 | 23 |
| 8.3 ± 0.2 | 23 |
| 8.4 ± 0.2 | 22 |
| 8.7 ± 0.2 | 24 |
| 10.3 ± 0.2 | 19 |
| 14.7 ± 0.2 | 30 |
| 21.2 ± 0.2 | 62 |
| 21.9 ± 0.2 | 59 |
| 22.4 ± 0.2 | 55 |
| 27.6 ± 0.2 | 45 |

* The relative intensities can change depending on the crystal size and morphology.

In one aspect, the crystalline form of Compound I is Form G.

H. Crystalline Form H

In one aspect, the present disclosure relates to a crystalline form of Compound I, characterized by an XRPD pattern having peaks at 3.8±0.2, 5.3±0.2, and 8.5±0.2 degrees two theta. In one aspect, the present disclosure relates to a crystalline form of Compound I, characterized by an XRPD pattern having peaks at 3.8±0.2, 5.3±0.2, 8.5±0.2, and 15.9±0.2 degrees two theta.

Figure 18:
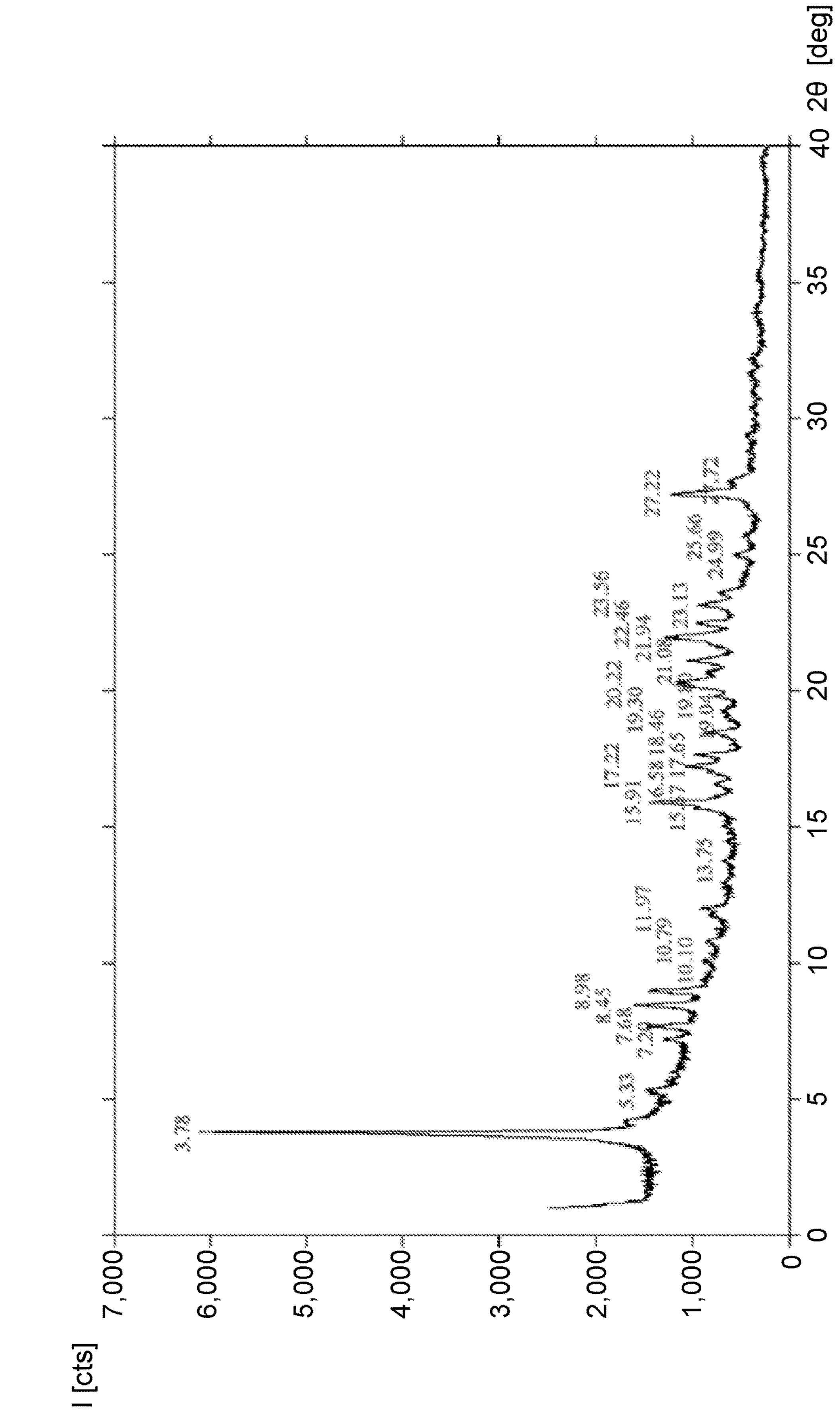
FIG. 18 is an XRPD corresponding to crystalline Form H.

In one aspect, the crystalline form of Compound I is characterized by an XRPD pattern substantially as shown in FIG. 18.

In one aspect, the crystalline form of Compound I is characterized by the following XRPD pattern in Table 10 expressed in terms of the degree 20 and relative intensities:

TABLE 10

| Angle (Degree 2θ) | Relative Intensity * (%) |
|---|---|
| 3.8 ± 0.2 | 100 |
| 5.3 ± 0.2 | 24 |
| 7.2 ± 0.2 | 21 |
| 7.7 ± 0.2 | 23 |
| 8.5 ± 0.2 | 26 |
| 9.0 ± 0.2 | 24 |
| 10.1 ± 0.2 | 15 |
| 10.8 ± 0.2 | 14 |
| 12.0 ± 0.2 | 14 |
| 13.8 ± 0.2 | 11 |
| 15.7 ± 0.2 | 16 |
| 15.9 ± 0.2 | 24 |
| 16.6 ± 0.2 | 13 |
| 17.2 ± 0.2 | 17 |
| 17.7 ± 0.2 | 16 |
| 18.5 ± 0.2 | 14 |
| 19.0 ± 0.2 | 11 |
| 19.3 ± 0.2 | 11 |
| 19.8 ± 0.2 | 12 |
| 20.2 ± 0.2 | 18 |
| 21.1 ± 0.2 | 16 |
| 21.9 ± 0.2 | 20 |
| 22.5 ± 0.2 | 15 |
| 23.1 ± 0.2 | 15 |
| 23.6 ± 0.2 | 12 |
| 25.0 ± 0.2 | 9 |
| 25.7 ± 0.2 | 8 |
| 27.2 ± 0.2 | 19 |
| 27.7 ± 0.2 | 10 |

* The relative intensities can change depending on the crystal size and morphology.

In one aspect, the crystalline form of Compound I is Form H.

I. Crystalline Form I

In one aspect, the present disclosure relates to a crystalline form of Compound I, characterized by an XRPD pattern having peaks at 5.0±0.2, 16.8±0.2, and 18.8±0.2 degrees two theta. In one aspect, the present disclosure relates to a crystalline form of Compound I, characterized by an XRPD pattern having peaks at 5.0±0.2, 15.9±0.2, 16.8±0.2, and 18.8±0.2 degrees two theta.

Figure 19:
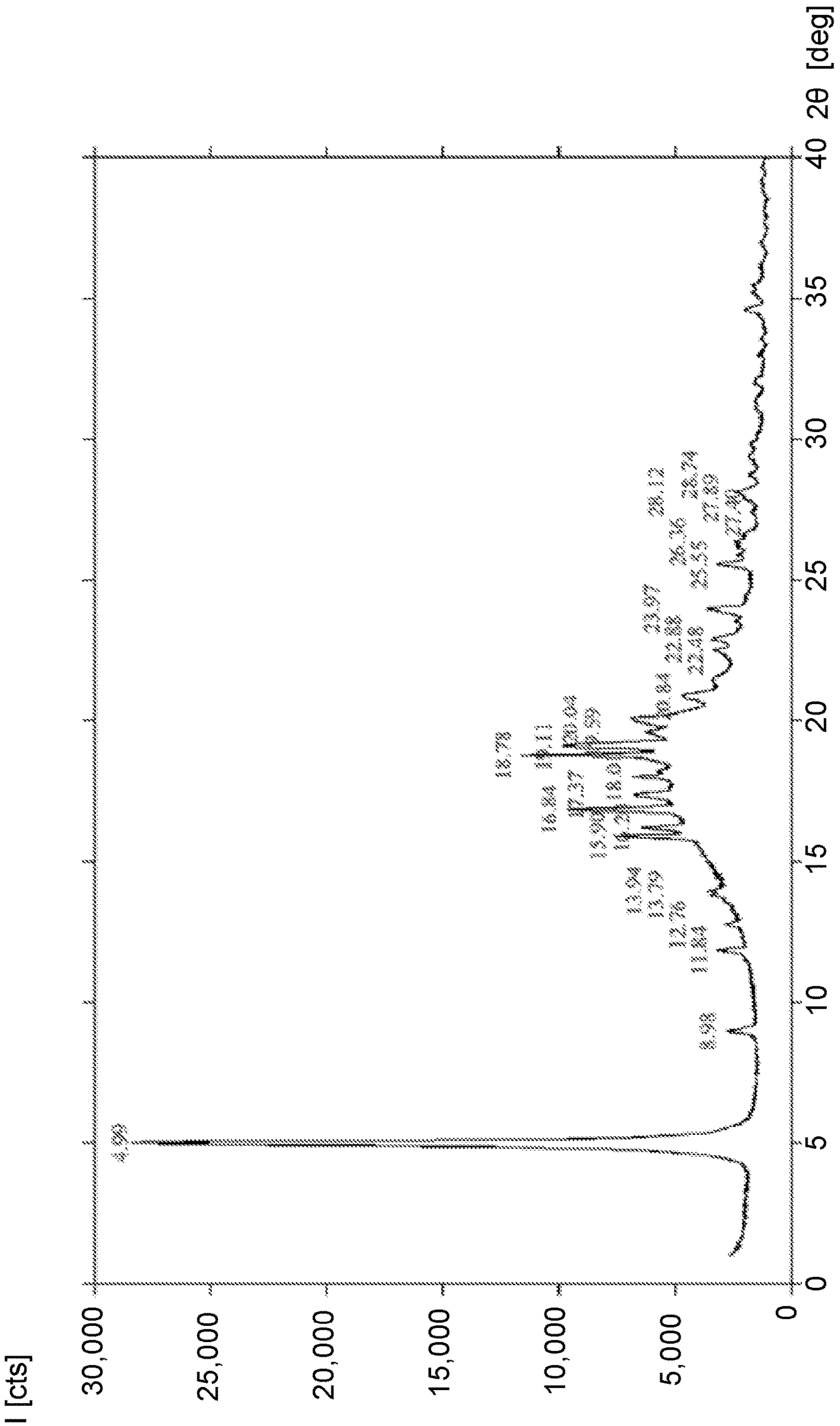
FIG. 19 is an XRPD corresponding to crystalline Form I.

In one aspect, the crystalline form of Compound I is characterized by an XRPD pattern substantially as shown in FIG. 19.

In one aspect, the crystalline form of Compound I is characterized by the following XRPD pattern in Table 11 expressed in terms of the degree 20 and relative intensities:

TABLE 11

| Angle (Degree 2θ) | Relative Intensity * (%) |
|---|---|
| 5.0 ± 0.2 | 100 |
| 9.0 ± 0.2 | 10 |
| 11.8 ± 0.2 | 11 |
| 12.8 ± 0.2 | 10 |
| 13.8 ± 0.2 | 12 |
| 13.9 ± 0.2 | 12 |
| 15.9 ± 0.2 | 27 |
| 16.2 ± 0.2 | 23 |
| 16.8 ± 0.2 | 34 |
| 17.4 ± 0.2 | 24 |
| 18.0 ± 0.2 | 24 |
| 18.8 ± 0.2 | 41 |
| 19.1 ± 0.2 | 35 |
| 19.6 ± 0.2 | 22 |
| 20.0 ± 0.2 | 24 |
| 20.8 ± 0.2 | 16 |
| 22.5 ± 0.2 | 12 |
| 22.9 ± 0.2 | 12 |
| 24.0 ± 0.2 | 12 |
| 25.6 ± 0.2 | 11 |
| 26.4 ± 0.2 | 9 |
| 27.4 ± 0.2 | 6 |

TABLE 11-continued

| Angle (Degree 2θ) | Relative Intensity * (%) |
|---|---|
| 27.9 ± 0.2 | 7 |
| 28.1 ± 0.2 | 8 |
| 28.7 ± 0.2 | 6 |

* The relative intensities can change depending on the crystal size and morphology.

In one aspect, the crystalline form of Compound I is Form I.

J. Crystalline Form J

In one aspect, the present disclosure relates to a crystalline form of Compound I, characterized by an XRPD pattern having peaks at 5.9±0.2, 17.4±0.2, and 18.8±0.2 degrees two theta. In one aspect, the present disclosure relates to a crystalline form of Compound I, characterized by an XRPD pattern having peaks at 5.9±0.2, 12.7±0.2, 17.4±0.2, and 18.8±0.2 degrees two theta.

Figure 20:
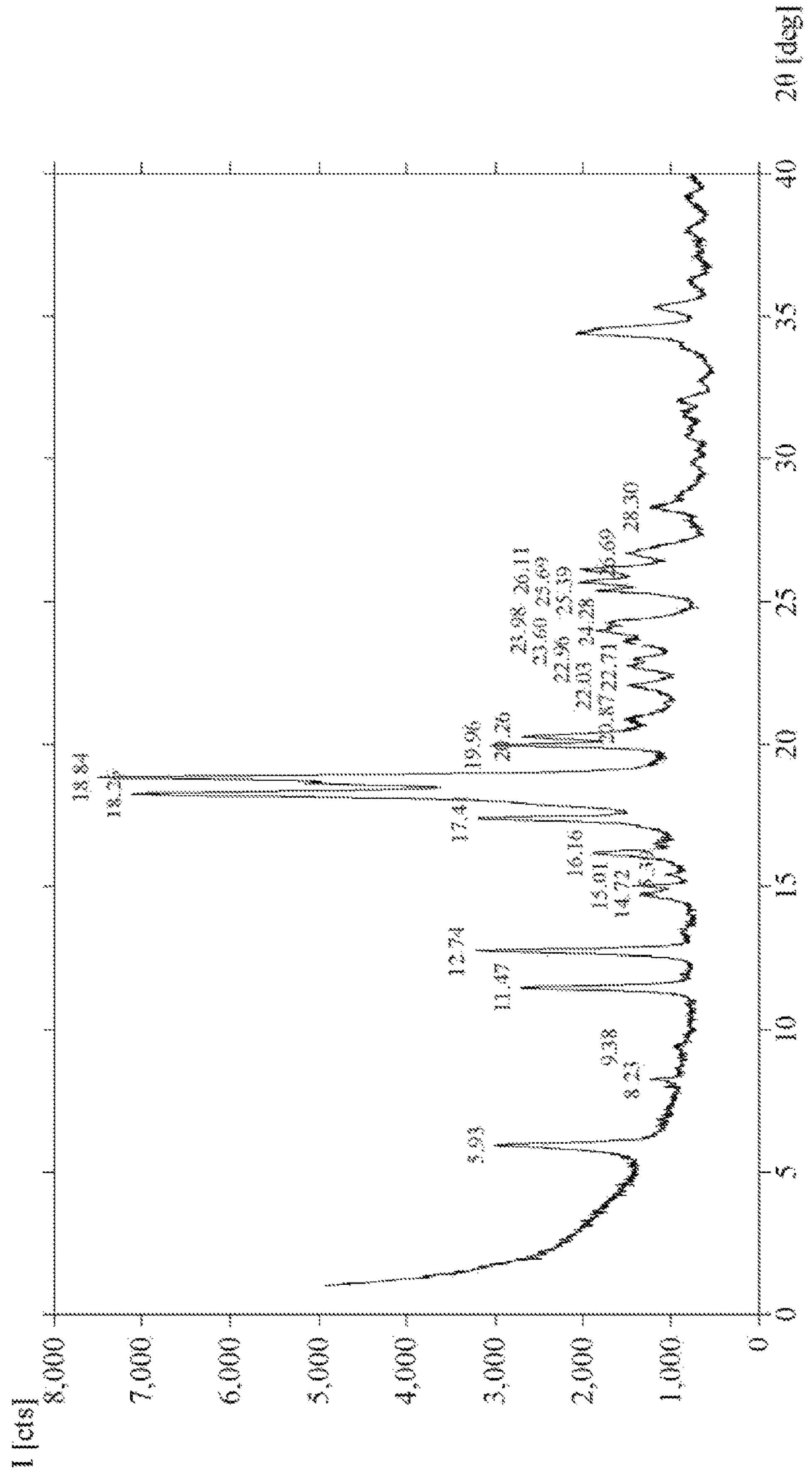
FIG. 20 is an XRPD corresponding to crystalline Form J.

In one aspect, the crystalline form of Compound I is characterized by an XRPD pattern substantially as shown in FIG. 20.

Figure 21A:
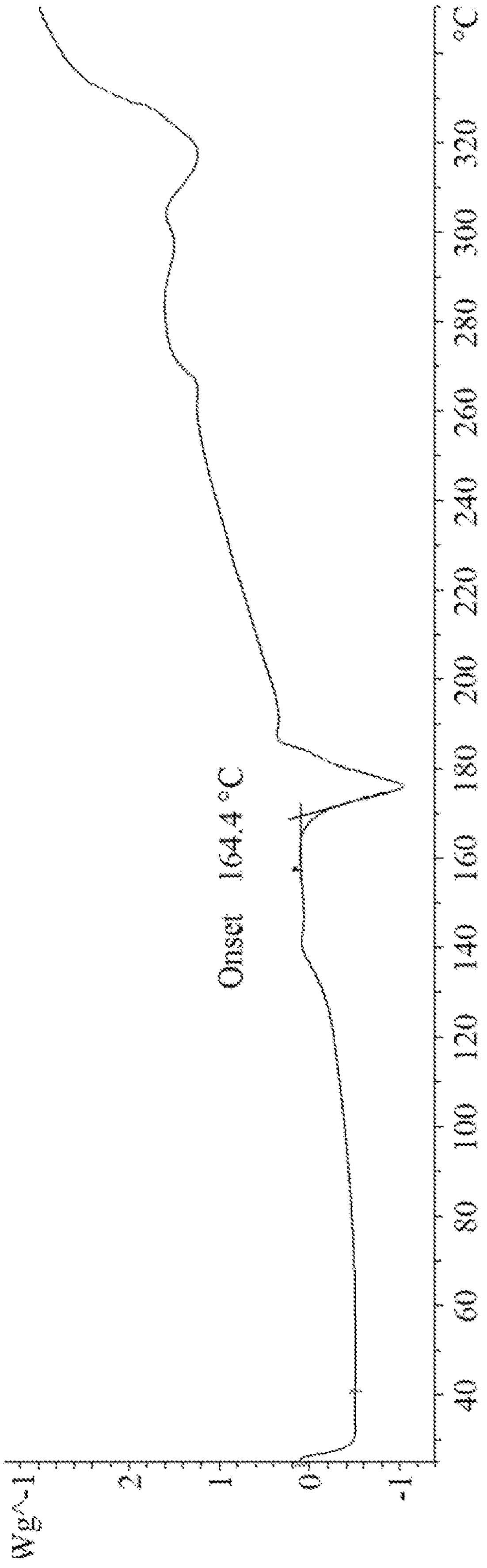
FIG. 21A is a DSC corresponding to crystalline Form J.
Figure 21B:
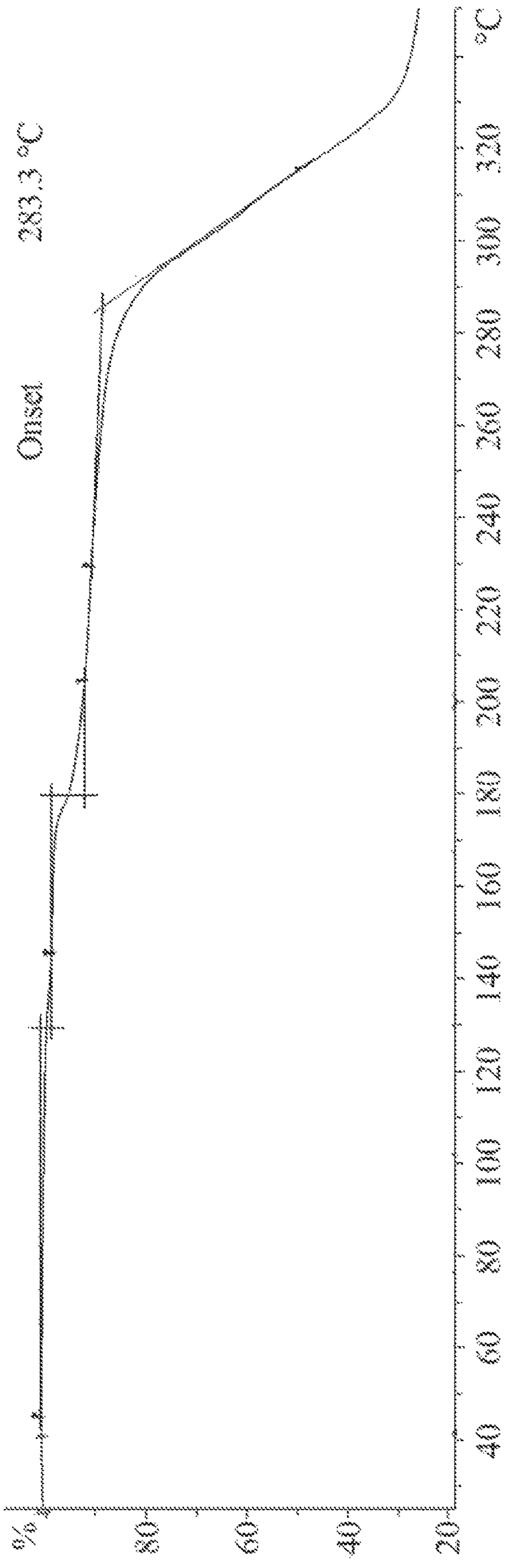
FIG. 21B is a TGA corresponding to crystalline Form J.

In one aspect, the crystalline form of Compound I is characterized by an endothermic peak with onset at about 164° C., as determined by DSC. In one aspect, the crystalline form of Compound I is characterized by a DSC profile substantially as shown in FIG. 21A. In one aspect, the crystalline form of Compound I is characterized by a TGA profile substantially as shown in FIG. 21B.

In one aspect, the crystalline form of Compound I is characterized by the following XRPD pattern in Table 12 expressed in terms of the degree 20 and relative intensities:

TABLE 12

| Angle (Degree 2θ) | Relative Intensity * (%) |
|---|---|
| 5.9 ± 0.20 | 40 |
| 8.2 ± 0.20 | 16 |
| 9.4 ± 0.20 | 13 |
| 11.5 ± 0.20 | 36 |
| 12.7 ± 0.20 | 42 |
| 14.7 ± 0.20 | 17 |
| 15.0 ± 0.20 | 19 |
| 15.4 ± 0.20 | 14 |
| 16.2 ± 0.20 | 25 |
| 17.4 ± 0.20 | 43 |
| 18.3 ± 0.20 | 93 |
| 18.8 ± 0.20 | 100 |
| 20.0 ± 0.20 | 41 |
| 20.3 ± 0.20 | 36 |
| 20.9 ± 0.20 | 20 |
| 22.0 ± 0.20 | 20 |
| 22.7 ± 0.20 | 20 |
| 23.0 ± 0.20 | 18 |
| 23.6 ± 0.20 | 20 |
| 24.0 ± 0.20 | 24 |
| 24.3 ± 0.20 | 22 |
| 25.4 ± 0.20 | 24 |
| 25.7 ± 0.20 | 27 |
| 26.1 ± 0.20 | 26 |
| 26.7 ± 0.20 | 20 |

* The relative intensities can change depending on the crystal size and morphology.

In one aspect, the crystalline form of Compound I is Form J.

In some aspects, any one of the crystalline forms discussed above is substantially free of other polymorphic forms. In some aspects, the crystalline form has a polymorphic purity of at least about 80%. In some aspects, the crystalline form has a polymorphic purity of at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%.

In one aspect, the crystalline form of Compound I is selected from the group consisting of Form A, Form B, Form C, Form D, Form E, Form F, Form G, Form H, Form I, and Form J. In one aspect, the crystalline form of Compound I is Form A.

In one aspect, the crystalline form of Compound I is a mixture of two or more forms selected from the group consisting of Form A, Form B, Form C, Form D, Form E, Form F, Form G, Form H, Form I, and Form J. In another aspect, the crystalline form of Compound I is a mixture of two or more forms selected from the group consisting of Form A, Form B, and Form C. In another aspect, the crystalline form of Compound I is a mixture of Form A and Form B, where Form B is the major form and Form A is the minor form.

In some aspects, the present disclosure provides a methods of making a crystalline form of Compound I where the crystalline form is selected from the group consisting of Form A, Form B, Form C, Form D, Form E, Form F, Form G, Form H, Form I, and Form J. One or more methods to prepare Forms A-J are provided in Experimental Section herein.

III. Pharmaceutical Composition

The present disclosure relates to a pharmaceutical composition comprising the crystalline form of any one of Forms A-J of Compound I and a pharmaceutically acceptable carrier, diluent, or excipients, or a mixture thereof.

In one aspect, the pharmaceutical composition comprises the crystalline form of any one of Forms A-J of Compound I.

Pharmaceutical compositions comprising the crystalline form of any one of Forms A-J of Compound I can be in a form suitable for oral use, for example, as tablets, troches, lozenges, dispersible powders or granules, or hard or soft capsules. Compositions intended for oral use can be prepared according to any known method, and such compositions can contain one or more agents selected from the group consisting of sweetening agents, flavoring agents, coloring agents, and preserving agents in order to provide pharmaceutically elegant and palatable preparations.

In some aspects, the pharmaceutical composition can be administered to subjects via the oral, parenteral (such as subcutaneous, intravenous, intramuscular, intrasternal and infusion techniques), rectal, intranasal, topical or transdermal (e.g., through the use of a patch) routes.

In one aspect, the pharmaceutical composition comprises about 100 mg to about 1500 mg, about 100 mg to about 1400 mg, about 100 mg to about 1300 mg, about 100 mg to about 1200 mg, about 100 mg to about 1100 mg, about 100 mg to about 1000 mg, about 100 mg to about 900 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 100 mg to about 150 mg of the crystalline form of any one of Forms A-J of Compound I disclosed herein. In one aspect, the pharmaceutical composition comprises about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg of the crystalline form of any one of Forms A-J of Compound I disclosed herein.

In some aspects, the pharmaceutical composition is an oral tablet. In some aspects, the oral tablet comprises about 0.1 mg to 2000 mg of the crystalline form of any one of Forms A-J 2-[3-cyclohexyl-3-(trans-4-propoxy-cyclohexyl)-ureido]-thiazol-5-ylsulfanyl}-acetic acid. In some aspects, the oral tablet comprises about 1 mg to about 2000 mg of the crystalline form of any one of Forms A-J of Compound I. In some aspects, the oral tablet comprises about 1 mg to about 1000 mg of the crystalline form of any one of Forms A-J of Compound I. In some aspects, the oral tablet comprises about 100 mg to about 800 mg of the crystalline form of any one of Forms A-J of Compound I. In some aspects, the oral tablet comprises about 50 mg to about 400 mg of the crystalline form of any one of Forms A-J of Compound I. In some aspects, the oral tablet comprises about 100 mg to about 400 mg of the crystalline form of any one of Forms A-J of Compound I. In some aspects, the oral tablet comprises about 100 mg to about 300 mg of the crystalline form of any one of Forms A-J of Compound I. In some aspects, the oral tablet comprises about 500 mg to about 1000 mg of the crystalline form of any one of Forms A-J of Compound I. In some aspects, the oral tablet comprises about 0.1 mg, about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, about 850 mg, about 900 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of the crystalline form of any one of Forms A-J of Compound I. In some aspects, the oral tablet comprises 800 mg of the crystalline form of any one of Forms A-J of Compound I. In some aspects, the oral tablet comprises 400 mg of the crystalline form of any one of Forms A-J of Compound I. In some aspects, the oral tablet comprises 300 mg of the crystalline form of any one of Forms A-J of Compound I. In some aspects, the oral tablet comprises about 200 mg of the crystalline form of any one of Forms A-J of Compound I.

IV. Method of Treatment

In some aspects, the present disclosure relates to a method of treating a type of diabetes mellitus, wherein the method comprises administering the pharmaceutical composition discussed above to a patient in need thereof. The method can comprise administering a pharmaceutical composition comprising a therapeutically effective amount of the crystalline form of any one of Forms A-J of Compound I. In some aspects, the type of diabetes mellitus is type 1 diabetes. In some aspects, the type of diabetes mellitus is type 2 diabetes. In some aspects, the type of diabetes is one or two types of type 1 diabetes and type 2 diabetes.

In some aspects, the patient is being treated with an insulin therapy. In some aspects, the insulin therapy is a continuous insulin infusion. In some aspects, the insulin therapy is a continuous subcutaneous insulin infusion. In some aspects, the insulin therapy is a multiple daily doses of insulin.

In another aspect, the present disclosure provides a method for the treatment of glucokinase-deficiency mediated conditions or diseases, or conditions benefiting from an increase in glucokinase activity, comprising administering to a subject in need thereof a compound or a pharmaceutical composition of the present disclosure.

In another aspect, the present disclosure provides a method for treatment of metabolic disorders, for blood glucose lowering, for the treatment of hyperglycemia, for the treatment of hypoglycemia for the treatment of impaired glucose tolerance (IGT), for the treatment of Syndrome X, for the treatment of impaired fasting glucose (IFG), for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behavior, or for enhancing the secretion of enteroincretins, comprising administering to a subject in need of such treatment a compound or a pharmaceutical composition of the present disclosure.

In another aspect, the present disclosure provides a method for the preservation of beta-cell mass and function comprising administering to a subject in need of such treatment a compound or a pharmaceutical composition of the present disclosure.

In another aspect, the present disclosure provides a method of preserving and/or increasing beta-cell mass and function in a subject having undergone pancreatic islet transplantation comprising administering to a subject in need of such treatment a compound or a pharmaceutical composition of the present disclosure.

In another aspect, the present disclosure provides a method of improving liver function and/or survival in subjects undergoing liver transplantation comprising administering to a subject in need of such treatment a compound or a pharmaceutical composition of the present disclosure. In a further aspect, the administration occurs before, during or after transplantation, or any combination thereof.

In another aspect, the present disclosure provides a method of preventing diabetic ketoacidosis or reducing the occurrence of diabetic ketoacidosis events in a subject comprising administering to a subject in need of such treatment a compound or a pharmaceutical composition of the present disclosure.

Depending on the condition, disorder, or disease to be treated and the subject's condition, the pharmaceutical compositions provided herein can be administered by oral, parenteral (e.g., intramuscular, intraperitoneal, intravenous or intraarterial (e.g., via catheter), ICV, intracistemal injection or infusion, subcutaneous injection, or implant), inhalation, nasal, vaginal, rectal, sublingual, and/or topical (e.g., transdermal or local) routes of administration, and can be formulated alone or together in suitable dosage unit with a pharmaceutically acceptable vehicle, carrier, diluent, excipient, or a mixture thereof, appropriate for each route of administration. In one aspect, the pharmaceutical composition is administered orally.

For oral administration, the pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions (e.g., aqueous or oil suspensions), wafers, sprinkles, elixirs, syrups, bolus, electuaries, or pastes. In one aspect, the pharmaceutical composition is administered as a tablet.

The dose can be in the form of one, two, three, four, five, six, or more sub-doses that are administered at appropriate intervals per day. The dose or sub-doses can be administered in the form of dosage units containing from about 1 mg to about 2000 mg, from about 10 mg to about 2000 mg, from about 100 mg to about 1500 mg, from about 200 mg to about 1500 mg, from about 200 mg to about 1500 mg, from about 300 mg to about 1500 mg, from about 400 mg to about 1500 mg, from about 500 mg to about 1500 mg, from about 500 mg to about 1000 mg, or from about 500 mg to about 800 mg of the crystalline form of any one of Forms A-J per dosage unit. For example, the dose or subdoses can be administered in the form of dosage units containing about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg of the crystalline form of any one of Forms A-J disclosed herein.

In some aspects, the patient is administered about 0.1 mg to about 2000 mg of the crystalline form of any one of Forms A-J of Compound I daily. In some aspects, the patient is administered about 1 mg to about 2000 mg of the crystalline form of any one of Forms A-J of Compound I daily. In some aspects, the patient is administered about 100 mg to about 800 mg of the crystalline form of any one of Forms A-J of Compound I daily. In some aspects, the patient is administered about 50 mg to about 400 mg of the crystalline form of any one of Forms A-J of Compound I daily. In some aspects, the patient is administered about 100 mg to about 400 mg of the crystalline form of any one of Forms A-J of Compound I daily. In some aspects, the patient is administered about 100 mg to about 300 mg of the crystalline form of any one of Forms A-J of Compound I daily. In some aspects, the patient is administered about 500 mg to about 1000 mg of the crystalline form of any one of Forms A-J of Compound I daily. In some aspects, the patient is administered about 0.1 mg, about 0.5 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 500 mg, about 550 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg, of the crystalline form of any one of Forms A-J of Compound I once daily. In some aspects, the patient is administered about 800 mg of the crystalline form of any one of Forms A-J of Compound I once daily. In some aspects, the patient is administered about 400 mg of the crystalline form of any one of Forms A-J of Compound I once daily. In some aspects, the patient is administered about 300 mg of the crystalline form of any one of Forms A-J of Compound I once daily. In some aspects, the patient is administered about 200 mg of the crystalline form of any one of Forms A-J of Compound I once daily. In some aspects, the patient is administered about 100 mg of the crystalline form of any one of Forms A-J of Compound I once daily.

EXAMPLES

A. Abbreviations and Acronyms

| | |
|---|---|
| DSC | Differential scanning calorimetry |
| DVS | Dynamic vapor sorption |
| HSM | Hot-stage microscopy |
| NMR | Nuclear magnetic resonance spectroscopy |
| PLM | Polarized light microscopy |
| TGA | Thermogravimetric analysis |
| XRPD | X-ray powder diffraction |
| CC | Crash cool |
| FC | Fast cool |
| FE | Fast evaporation |
| SAS | Solvent/antisolvent |
| SE | Slow evaporation |
| ACN | Acetonitrile |
| 1-BuOH | 1-Butanol |
| 2-BuOH | 2-Butanol |
| BuOAc | Butyl acetate |
| iBuOAc | Isobutyl acetate |
| t-BuOAc | tert-Butyl acetate |
| $CHCl_3$ | Chloroform |
| DCE | 1,2-Dichloroethane |
| DCM | Dichloromethane |
| DMF | Dimethylformamide |
| DMSO | Dimethyl sulfoxide |
| EtOAc | Ethyl acetate |
| EtOH | Ethanol |
| HFIPA | Hexafluoroisopropanol or Hexafluoro-2-propanol |
| H2O | Water |
| IPA | Isopropyl alcohol or 2-propanol |
| MEK | Methyl ethyl ketone or butanone |
| MeOH | Methanol |
| MIBK | Methyl isobutyl ketone |
| MTBE | Methyl tert-butyl ether |
| NMP | N-Methyl-2-Pyrrolidone |
| iPrOAc | Isopropyl acetate |
| 1-PrOH | 1-Propanol |
| TFE | 2,2,2-Trifluoroethanol |
| THF | Tetrahydrofuran |
| agg. | Aggregates |
| anh. | Anhydrous |
| B/E | Birefringence and extinction |
| d | Day(s) |
| endo | Endotherm |
| h | hour(s) |
| min | minute(s) |
| NA | numerical aperture |
| RH | Relative humidity |
| RT | Room temperature/ambient temperature |
| UM | Unknown morphology |
| v/v | Volume/volume |
| w/ | With |
| wt | Weight |

B. Experimental Methods

Example 1: Stable Form and Hydrate Screen Via Slurry-Trituration Experiments Slurry triburation experiments target the stable forms, including stable solvates and hydrates.

The slurry-trituration experiments were conducted by stirring solids of Compound I in specified solvents and solvent mixtures at various temperatures for 7 days (elevated temperature) or 14-18 days (ambient and sub-ambient temperatures). A summary of experimental conditions and results is detailed in Table 13.

TABLE 13

| Solvent (v/v) | Condition * | Observations | XRPD Result |
|---|---|---|---|
| $CHCl_3$ | 2-8° C., 18 d | white suspension, B/E particles & agg., UM | Form H |
| dioxane/ $H_2O$ (85/15) | 2-8° C., 18 d | white suspension, B/E particles & agg., UM | Form A |
| HFIPA/ MTBE (50/50) | 2-8° C., 18 d | white suspension, B/E particles & agg., UM | Form A |
| TFE/$H_2O$ (87/13) | 2-8° C., 18 d | white suspension, B/E particles & agg., UM | Form A |
| THF/$H_2O$ (93/7) | 2-8° C., 18 d | white suspension, B/E particles & agg., UM | Form A |
| acetone | RT, 14 d | yellow suspension, B/E particles & agg., UM | Form A |
| 2-BuOH | RT, 14 d | white suspension, B/E particles & agg., UM | Form A |
| DCM | RT, 14 d | brown suspension, B/E particles & agg., UM | Form C, w/ extra peaks at 2.8° and 8.6° 2θ |
| DMSO/ iPrOAc (5/95) | RT, 14 d | white suspension, B/E particles & agg., UM | Form A |
| dioxane | RT, 14 d | white suspension, B/E particles & agg., UM | Form A |
| EtOH | RT, 14 d | white suspension, B/E particles & agg., UM | Form A |
| MEK | RT, 14 d | white suspension, B/E particles & agg., UM | Form A |
| MeOH | RT, 14 d | white suspension, B/E particles & agg., UM | Form A |
| NMP: nitromethane (20/80) | RT, 14 d | white suspension, B/E particles & agg., UM | Form A |
| 1-PrOH | RT, 14 d | white suspension, B/E particles & agg., UM | Form A |
| TFE | RT, 14 d | white suspension, B/E particles & agg., UM | Form A |
| THF | RT, 14 d | off white suspension, B/E particles & agg., UM | Form A |
| anh. ACN | 55° C., 7 d | white suspension, B/E particles & agg., UM | Form A |
| anh. DCE | 55° C., 7 d | light yellow suspension, B/E particles & agg., UM | Form A |
| anh. EtOAc | 55° C., 7 d | white suspension, B/E particles & agg., UM | Form A |
| anh. EtOH | 55° C., 7 d | brown suspension, B/E particles & agg., UM | decomposed |
| anh. toluene | 55° C., 7 d | white suspension, B/E particles & agg., UM | Form A |

* Temperatures are approximate.

Example 2: Polymorph Screen

Solids of Compound I unless noted otherwise, was used as the starting material. Materials produced in the study were utilized for selected experiments.

Method a: Evaporation Experiments

Solutions of starting material were allowed to partially evaporate or evaporate to dryness at ambient or elevated temperature from open vials for fast evaporation (FE) or from vials covered with aluminum foil with pin holes for slow evaporation (SE). Prior to evaporation, solutions were filtered at ambient or elevated temperature using 0.2 µm nylon filters.

Method b: Cooling Experiments

Solutions of starting material were prepared in specified solvents at elevated temperature using a hot plate for heating. These were typically hot-filtered through a 0.2 µm nylon filter into warm receiving vials. The vials were either quickly transferred into a sub-ambient temperature bath (typically dry ice/acetone) for crash cooling (CC), removed from the hot place for fast cooling (FC) or the heat was turned off to allow for slow cooling (SC). If solids precipitated, they were isolated cold by vacuum filtration. If the solution remained clear, the sample was either kept at sub-ambient temperatures or further crystallization techniques were applied.

Method c: Slurry Experiments

Solids were suspended in specified solvents. The suspensions were then agitated at ambient or set temperature. After a given amount of time solids were isolated.

Method d: Solvent/Anti-Solvent Precipitation

Solutions of starting material were prepared at ambient or elevated temperature and filtered using 0.2 µm nylon filters. They were then mixed with appropriate anti-solvents at elevated temperature. If no solids were observed, the samples were either cooled to ambient or sub-ambient temperatures or other crystallization techniques applied.

Polymorph screening was performed using various solvent-based techniques including evaporation, cooling, slurry, solvent/anti-solvent addition, and combinations of these techniques. Detailed experimental conditions, observations, and XRPD results are summarized in Table 14.

TABLE 14

| Solvent (v/v) | Conditions * | XRPD Result |
|---|---|---|
| Acetone | 1. SE then FE | Form A + Form B, w/ an extra peak at 5.9° 2θ |
| | 1. FC (55° C. to an ice/water bath)<br>2. kept at −10∼−25° C. for 4 d | Form B + minor Form A, w/extra peaks at 5.9° and 18.3° 2θ |
| | slurry, seeded w/8065-30-03, RT for 7 d | Form A |
| anh. Acetone | 1. CC (55° C. to −78° C.)<br>2. vial inside wall scratched for nucleation, kept at −10∼−25° C. for 3 d | Form B + minor Form A |
| acetone/$H_2O$ (68/32) | 1. SAS, API solution in acetone into cold $H_2O$<br>2. kept in ice/water bath for 1 h<br>3. kept at −10∼−25° C. for 1 d | Form E + Form A |
| 2-BuOH | 1. FC (55° C. to an ice/water bath)<br>2. kept at −10∼−25° C. for 11 d | Form A |
| iBuOH/ t-BuOAc (2/1) | 1. SAS, API solution in iBuOH in ice/water bath, added t-BuOAc to API solution<br>2. kept at −10∼−25° C. for 7 d | — |
| $CHCl_3$ | SE | disordered |
| DCE | 1. FC (55° C. to an ice/water bath)<br>2. kept at −10∼−25° C. for 11 d<br>3. stirred at RT for 3 d<br>4. FE (partial), stirred at RT for 5 d<br>5. FE (partial) | Form A |
| DCM | SE | Form D + additional phase(s) |
| | CC (RT to −78° C.) | disordered |
| | slurry, 2-8° C. for 6 d | Form H |
| DMF/MTBE (3/97) | 1. SAS, API solution in DMF into MTBE at RT<br>2. kept at −10∼−25° C. for 20 d | disordered, Form A + additional phase(s) |
| dioxane/ DMSO | 1. FC (55° C. to an ice/water bath)<br>2. kept at 2-8° C. for 11 d | Form A |
| | 1. solids in dioxane heated | Form A |

TABLE 14-continued

| Solvent (v/v) | Conditions * | XRPD Result |
|---|---|---|
| | to 55° C.<br>2. added DMSO at 55° C.<br>3. FC in ice/water bath<br>4. kept at 2-8° C. for 7 d | |
| dioxane/$H_2O$ (1/1) | 1. SAS, API solution in dioxane into cold $H_2O$<br>2. stirred at 2-8° C. for 1 d | Form A |
| EtOAc/ HFIPA | 1. solids in EtOAc heated to 55° C.<br>2. added HFIPA (36:64), stirred at 60° C., 1 d<br>3. FC (60° C. to an ice/water bath)<br>4. FE, w/$N_2$ purge | decomposed |
| EtOH | 1. FC (55° C. to an ice/water bath)<br>2. kept at −10∼−25° C. for 11 d | Form B + minor Form A |
| | 1. CC (55° C. to −78° C.)<br>2. vial inside wall scratched for nucleation, kept at −10∼−25° C. for 3 d | Form B w/an extra peak at 5.9° 2θ |
| HFIPA | SE | Form F |
| HFIPA/ EtOAc, anh. (1/25) | 1. SAS, API solution in HFIPA into EtOAc<br>2. vial inside wall scratched for nucleation, kept at −10∼−25° C. for 3 d | Form I |
| MEK/ BuOAc, anh. (1/1) | 1. SAS, API solution in MEK into BuOAc<br>2. kept at −10∼−25° C. for 7 d<br>3. FE, RT | Form E |
| MEK/ Methylcyclo hexane (2/1) | 1. SAS, API solution in MEK kept in ice/water bath, added methylcyclohexane to API solution<br>2. kept at −10∼−25° C. for 3 d<br>3. FE under $N_2$ purge for 2 h | Form I w/peak shifts |
| MeOH/ nitromethane (1/1) | 1. SAS, API solution in MeOH in ice/water bath, nitromethane added to API solution<br>2. FE (partial), RT<br>3. FE under $N_2$ purge for 1 h | Form E + Form A + additional phase(s) |
| MeOH/ iBuOAc (2/1) | 1. SAS, API solution in MeOH into iBuOAc at RT<br>2. kept at −10∼−25° C. for 7 d<br>3. FE, RT | Form E + additional phase(s) |
| NMP/PrOAc (5/95) | 1. API solution in NMP added to PrOAc<br>2. kept at −10∼−25° C. for 7 d | — |
| iPrOAc/ NMP | 1. solids in iPrOAc, heated to 55° C.<br>2. added NMP at 55° C.<br>3. FC in ice/water bath<br>4. kept at −10∼−25° C. for 7 d | — |
| 1-PrOH/ DMSO | 1. solids in 1-PrOH heated to 60° C.<br>2. added DMSO<br>3. FC to RT<br>4. kept at −10∼−25° C. for 20 d | Form A |
| TFE | FE | Form G |
| toluene/ DMSO anh. | 1. solids in toluene heated to 45° C.<br>2. added anh DMSO at 45° C.<br>3. FC in ice/water bath<br>4. added additional anh. toluene<br>5. kept at −10∼−25° C. for 7 d | — |
| THF/$H_2O$ (93/7) | 1. FE<br>2. air-dried on filter paper | Form A |

* Times and temperatures are approximate.

Example 3: Preparation of Selected Materials

Table 15 summarizes the preparation conditions for selected materials.

TABLE 15

| Solvent | Conditions * | XRPD Result |
|---|---|---|
| anh. acetone | 1. FC (55° C. to ice/water bath)<br>2. kept at −10∼−25° C. for 5 d<br>3. FE (partial) under $N_2$ purge, RT<br>4. kept at −10∼−25° C. for 4 h<br>5. dried under vacuum at 45° C. for 1 d | Form E |
| DCM | 1. slurried at RT for 9 d<br>2. air-dried at RT for 1 h<br>3. dried under vacuum at 45° C. for 4 h | Form D |
| EtOH | 1. FC (55° C. to ice/water bath)<br>2. kept at −10∼−25° C. for 5 d<br>3. solids isolated, dried under vacuum at 45° C. for 4 h | Form B, w/extra peak at 5.9° 2θ |

* Times and temperatures are approximate.

Table 16 summarizes the drying conditions for selected materials

TABLE 16

| Material | Condition * | XRPD Results |
|---|---|---|
| Compound I Form F | vacuum/45° C./3 d | Compound I Form D |
| Compound I Form G | vacuum/45° C./3 d | disordered |
| Compound I Form E + minor Form A | vacuum/45° C./1 d | Compound I Form B + minor Form A |
| Compound I Material G | vacuum/45° C./1 d | disordered |
| Compound I Form C | vacuum/45° C./1 d | Compound I Form D ± additional peak |
| | vacuum/45° C./1 h | Compound I Form D |
| Compound I Form I | vacuum/45° C./1 d | Compound I Form B |
| Compound I Form I w/ peak shifts | vacuum/45° C./2 d | similar to Compound I Form B |

* Times and temperatures are approximate.

Example 4: Competitive Slurry Experiment

In order to identify the thermodynamically most stable anhydrous form among Form A, Form D, Form B, and Form E, competitive slurries were performed in acetone at 2-8° C., ambient temperature, and 45° C.

At each condition, similar amounts of solids from the four forms/materials were slurried in pre-saturated solutions at the examined temperature conditions for 7 days; solids were then isolated and analyzed wet by XRPD. The detailed experimental conditions and XRPD results are summarized in Table 17.

TABLE 17

| Materials | Solvent * | Condition ** | XRPD Results |
|---|---|---|---|
| 9 mg Form A<br>6 mg Form D<br>7 mg Form B<br>6 mg Form E | acetone | 2-8° C., 7 d | Form A |
| 9 mg Form A<br>7 mg Form D | acetone | RT, 7 d | Form A |

TABLE 17-continued

| Materials | Solvent * | Condition ** | XRPD Results |
|---|---|---|---|
| 7 mg Form B<br>5 mg Form E<br>9 mg Form A<br>8 mg Form D<br>6 mg Form B<br>7 mg Form E | acetone | 45° C., 7 d | Form A |

* Solutions were pre-saturated with Form A at each condition.

** Times and temperatures are approximate.

X-Ray Powder Diffraction (XRPD)

XRPD patterns were collected with a PANalytical X'Pert PRO MPD or Empyrean diffractometer using an incident beam of Cu radiation produced using an Optix long, fine-focus source. An elliptically graded multilayer mirror was used to focus Cu Kα X-ray radiation through the specimen and onto the detector. Prior to the analysis, a silicon specimen (NIST SRM 640e) was analyzed to verify the observed position of the Si (111) peak is consistent with the NIST-certified position. A specimen of the sample was sandwiched between 3-μm-thick films and analyzed in transmission geometry. A beam-stop, short antiscatter extension, and antiscatter knife-edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5.

Thermogravimetric Analysis and Differential Scanning Calorimetry Combination Analyses (TGA/DSC)

TGA/DSC combination analyses were performed using a Mettler Toledo TGA/DSC3+ analyzer. Temperature and enthalpy adjustments were performed using indium, tin, and zinc, and then verified with indium. Balance was verified with calcium oxalate. The sample was placed in an aluminum pan. The pan was hermetically sealed, the lid pierced, then inserted into the TG furnace. A weighed aluminum pan configured as the sample pan was placed on the reference platform. The furnace was heated under nitrogen.

Dynamic Vapor Sorption (DVS)

Moisture sorption/desorption data were collected on a Surface Measurement System DVS Intrinsic instrument. Samples were not dried prior to analysis. For the as received lot, sorption and desorption data were collected over a range from 5% to 95% RH at 10% RH increments. The equilibrium criterion used for analysis was less than 0.0100% weight change in 5 minutes with a maximum equilibration time of 3 hours. Data were not corrected for the initial moisture content of the samples.

Hot Stage Microscopy (HSM)

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective, 0.40 NA with crossed polarizers and a first order red compensator. Images were captured using SPOT software (v. 4.5.9).

Polarized Light Microscopy (PLM)

PLM was performed using a Leica DM LP microscope equipped with a Spot Insight color camera. Crossed-polarized light was used with a first order red compensator. Various objectives were used to view the sample. Samples were suspended either in mineral oil or the dispersant selected for the method. Images were acquired at ambient temperature using Spot Advanced software (v.4.5.9). Micrometer bars were inserted onto the images as a reference for size. Particle sizes were measured using an eyepiece reticle scale calibrated using a NIST traceable stage micrometer.

Proton Solution Nuclear Magnetic Resonance Spectroscopy ($^1$H NMR)

The solution NMR spectra were acquired with a Bruker AVANCE 600 MHz Spectrometer using DMSO-$d_6$.

Carbon-13 Solid State Nuclear Magnetic Resonance Spectroscopy ($^{13}$C solid state NMR)

The $^{13}$C solid-state cross polarization magic angle spinning (CP/MAS) NMR spectrum was acquired at ambient temperature on an Agilent DD2-400 spectrometer (Larmor frequencies: $^{13}$C=100.549 MHz, $^1$H=399.812 MHz). The sample was packed into a 4 mm PENCIL type zirconia rotor and rotated at 12 kHz at the magic angle. The spectrum was acquired with phase modulated (SPINAL-64) high power $^1$H decoupling during the acquisition time using a $^1$H pulse width of 2.6 μs (90°), a ramped amplitude cross polarization contact time of 5 ms, a 30 ms acquisition time, a 10 second delay between scans, a spectral width of 45 kHz with 2678 data points, and 1600 co-added scans. The free induction decay (FID) was processed using Agilent VnmrJ 3.2A software with 65536 points and an exponential line broadening factor of 10 Hz to improve the signal-to-noise ratio. The first three data points of the FID were back predicted using the VNMR linear prediction algorithm to produce a flat baseline. The chemical shifts of the spectral peaks were externally referenced to the carbonyl carbon resonance of glycine at 176.5 ppm.

Infrared Spectroscopy (IR)

The IR spectrum was acquired using a Nicolet 6700 Fourier transform infrared (FT-IR) spectrophotometer (Thermo Nicolet) equipped with an Ever-Glo mid/far IR source, a potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech) equipped with a germanium (Ge) crystal was used for data acquisition. The spectrum represents 256 co-added scans collected at a spectral resolution of 4 $cm^{-1}$. A background data set was acquired with a clean Ge crystal. A Log 1/R (R=reflectance) spectrum was obtained by taking a ratio of these two data sets against each other.

XRPD Indexing

The high-resolution XRPD pattern of Compound I was indexed using X'Pert High Score Plus 2.2a (2.2.1) in this study. Indexing and structure refinement are computational studies. Agreement between the allowed peak positions, marked with red bars, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated below each figure showing tentative indexing solution. To confirm the tentative indexing solution, the molecular packing motifs within the crystallographic unit cells must be determined. No attempts at molecular packing were performed.

CONCLUSION

Multiple crystalline materials of Compound I were observed in this study, including Forms A-J.

Forms A, B, D, and E are anhydrous materials of Compound I. Among them, Form A is likely the most stable form within 2-8° C. to 45° C. based on results from competitive slurries.

Form C is likely a DCM solvate which desolvates into Form D. Form F is also a solvated material and converts to Form D upon drying.

Form I could represent a family of iso-structural solvates. It converts to Form E or solids similar to Form E upon drying.

Forms G and H are disordered crystalline materials and could be solvates. They become disordered upon drying.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

What is claimed is:

1. An anhydrous crystalline form of {2-[3-cyclohexyl-3-(trans-4-propoxy-cyclohexyl)-ureido]-thiazol-5-ylsulfanyl}-acetic acid that is characterized as having:

an X-ray powder diffraction (XRPD) comprising peaks at the following diffraction angles: 11.0+0.2, 11.6 +0.2, and 17.8 +0.2 degrees two theta as measured using Cu, Kα radiation (Form B); and (i) an endothermic peak with onset at about 166° C., as determined by Differential Scanning Calorimetry (DSC), or (ii) an Infrared Spectroscopy (IR) pattern having peaks at 1310.1±2.0, 1514.4±2.0, and 1661.3±12.0$cm^{-1}$; and a polymorphic purity of at least 95%; or an XRPD comprising peaks at the following diffraction angles: 5.3±0.2, 8.7±0.2, and 26.4±0.2 degrees two theta as measured using Cu, Kα radiation (Form D); an endothermic peak with onset at about 147° C., as determined by DSC; and a polymorphic purity of at least 95%; or an XRPD comprising peaks at the following diffraction angles: 5.8±0.2, 17.9±0.2, and 18.9±0.2 degrees two theta as measured using Cu, Kα radiation (Form E); an endothermic peak with onset at about 171° C., as determined by DSC; and a polymorphic purity of at least 95%.

2. A crystalline form of {2-[3-cyclohexyl-3-(trans-4-propoxy-cyclohexyl)-ureido]-thiazol-5-ylsulfanyl}-acetic acid comprising Crystalline Form A and either Crystalline Form B or Crystalline Form E, wherein Crystalline Form A is characterized as having an X-ray powder diffraction (XRPD) comprising peaks at the following diffraction angles: 8.7±0.2, 16.9±0.2, 17.4±0.2, and 20.1±0.2 degrees two theta as measured using Cu, Kα radiation (Form A); and an endothermic peak with onset at about 160° C., as determined by Differential Scanning Calorimetry (DSC);

wherein Crystalline Form B is characterized as having an XRPD comprising peaks at the following diffraction angles: 11.0±0.2, 11.6±0.2, 17.8±0.2, and 21.1±0.2 degrees two theta as measured using Cu, Kα radiation (Form B); and an endothermic peak with onset at about 166° C., as determined by DSC; and wherein Crystalline Form E is characterized as having an XRPD comprising peaks at the following diffraction angles: 5.8±0.2, 17.9±0.2, 18.9±0.2, and 20.7±0.2 degrees two theta as measured using Cu, Kα radiation (Form E); and an endothermic peak with onset at about 171° C., as determined by DSC.

3. The anhydrous crystalline form of claim 1, wherein {2-[3-cyclohexyl-3-(trans-4-propoxy-cyclohexyl)-ureido]-thiazol-5-ylsulfanyl}-acetic acid is characterized as having an XRPD comprising peaks at the following diffraction angles: 11.0±0.2, 11.6±0.2, and 17.8±0.2 degrees two theta as measured using Cu, Kα radiation (Form B); and (i) an endothermic peak with onset at about 166° C., as determined by DSC, or (ii) an IR pattern having peaks at 1310.1±2.0, 1514.4±2.0, and 1661.3±2.0 $cm^{-1}$.

4. The anhydrous crystalline form of claim 1, wherein {2-[3-cyclohexyl-3-(trans-4-propoxy-cyclohexyl)-ureido]-thiazol-5-ylsulfanyl}-acetic acid is characterized as having an XRPD comprising peaks at the following diffraction angles: 5.3±0.2, 8.7±0.2, and 26.4±0.2 degrees two theta as measured using Cu, Kα radiation (Form D); and an endothermic peak with onset at about 147° C., as determined by DSC.

5. The anhydrous crystalline form of claim 1, wherein {2-[3-cyclohexyl-3-(trans-4-propoxy-cyclohexyl)-ureido]-thiazol-5-ylsulfanyl}-acetic acid is characterized as having an XRPD comprising peaks at the following diffraction angles: 5.8±0.2, 17.9±0.2, and 18.9±0.2 degrees two theta as measured using Cu, Kα radiation (Form E); and an endothermic peak with onset at about 171° C., as determined by DSC.

* * * * *